United States Patent [19]

Crawford et al.

[11] Patent Number: 5,661,108
[45] Date of Patent: Aug. 26, 1997

[54] HERBICIDAL 3-(BICYCLIC NITROGEN-CONTAINING HETEROCYCLE)-SUBSTITUTED-1-METHYL-6-TRIFLUOROMETHYLURACILS

[75] Inventors: Scott D. Crawford, Plainsboro; Lester L. Maravetz, Westfield; George Theodoridis, Princeton, all of N.J.

[73] Assignee: FMC Corporation, Philadelphia, Pa.

[21] Appl. No.: 375,447

[22] Filed: Jan. 18, 1995

Related U.S. Application Data

[63] Continuation-in-part of Ser. No. 252,519, Jun. 1, 1994, abandoned.

[51] Int. Cl.[6] .................... C07D 403/02; A01N 43/54
[52] U.S. Cl. ............................ 504/243; 544/310
[58] Field of Search ..................... 504/243; 544/310

[56] References Cited

PUBLICATIONS

Chemical Abstracts, vol. 81, Entry 78475a (1974).
Narr et al, Chemical Abstracts, vol. 117, Entry 48554v (1992).

*Primary Examiner*—John M. Ford
*Attorney, Agent, or Firm*—H. Robinson Ertelt; Robert M. Kennedy

[57] ABSTRACT

Herbicidal 3-(bicyclic nitrogen-containing heterocycle)-substituted-1-methyl-6-trifluoromethyluracils, compositions containing them, and methods of using them to control undesired plant growth are disclosed. The herbicidal compounds of the present invention are defined by the following generic structure:

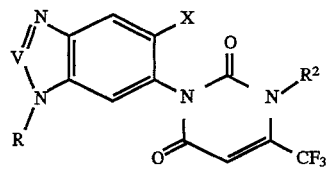

in which V is N or C—$R^1$; R is hydrogen, straight or branched chain alkyl, alkenyl, alkynyl, hydroxyalkyl, alkoxyalkyl, haloalkyl, alkoxycarbonylalkyl, arylalkyl, optionally substituted with halogen, or aminocarbonylalkyl in which the amino nitrogen is substituted with arylalkyl or one or two alkyl; $R^1$ is hydrogen, alkyl, haloalkyl, or cyano; $R^2$ is lower alkyl or amino; and X is hydrogen or halogen, with the proviso that each aliphatic component has not more than six carbon atoms.

21 Claims, No Drawings

HERBICIDAL 3-(BICYCLIC NITROGEN-CONTAINING HETEROCYCLE)-SUBSTITUTED-1-METHYL-6-TRIFLUOROMETHYLURACILS

This is a continuation-in-part of application Ser. No. 252,519, filed Jun. 1, 1994, now abandoned.

The invention described in this application pertains to weed control in agriculture, horticulture, and other fields where there is a desire to control unwanted plant growth. More specifically, the present application describes certain herbicidal 3-(bicyclic nitrogen-containing heterocycle)-substituted 1-methyl-6-trifluoromethyluracils, in which the heterocycles are benzimidazoles or benztriazoles, as well as compositions containing them, methods of preparing them, and methods for preventing or destroying undesired plant growth by preemergence or postemergence application of herbicidal compositions to the locus where control is desired. The herbicidal activity of the present compounds has not previously been described.

The use of uracils as herbicides has previously been reported. U.S. Pat. Nos. 3,235,357, 3,235,358, 3,235,360, 3,235,361, 3,235,363, 3,352,862, 3,352,863, 3,3600,521, and 3,360,522 all disclose and claim a wide variety of substituted uracils for use as herbicides. Of these, only 3,235,363 discloses uracils with a substituent in the 1-position, and none discloses a uracil with a heterocycle in the 3-position.

More recent publications disclose herbicidal uracils having a heterocyclic substituent. German Offenlegungsschrift DE 3819823 A1 discloses indole, indazole, or benzimidazole derivatives of the following structure as useful as pre- or postemergence selective herbicides:

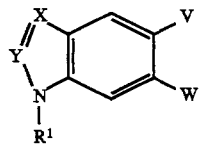

in which both V is hydrogen, fluoro, chloro, or a range of amino derivatives, and $R^1$ and W are very broadly defined. $R^1$ may be any one of a number of optionally substituted aliphatic groups; W may be any one of eleven different heterocycles, each generically defined, including

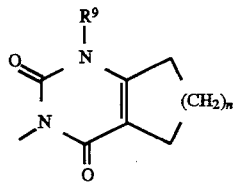

in which n is 1 or 2; and $R^9$ is hydrogen, optionally halogen-substituted 1–5C alkyl, or 3–5C alkenyl, or 3–5C alkynyl.

European Patent Application EP 438209A discloses the following aryl-substituted uracil derivatives as herbicides:

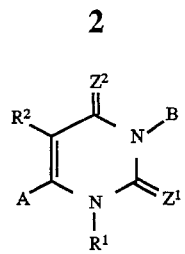

in which $R^1$ and $R^2$ are broadly defined and may be hydrogen or haloalkyl; $Z^1$ and $Z^2$ are oxygen, sulfur, or imino; and A and B are very broadly defined, each being an aryl group or one of a large number of heterocycles, including benzoxazolyl and benzothiazolyl, all optionally substituted.

Japanese Patent Application JO 3287-585A discloses the following aryl-substituted uracil derivatives as herbicides:

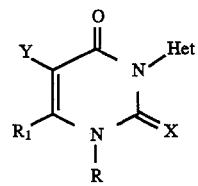

in which X is oxygen or sulfur; Y may be hydrogen, inter alia; $R_f$ and R are haloalkyl; and Het is a 5- or 6- membered heterocyclyl containing at least one nitrogen, oxygen, and/or sulfur atom. The only disclosed benzoheterocycle is bonded to the uracil ring through the heterocycle, not through the benzene ring.

U.S. Pat. No. 5,169,431 discloses benzofuranyl derivatives of uracil having the following structure as herbicides:

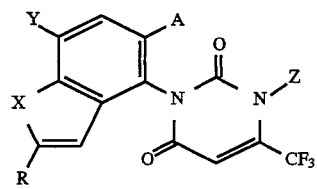

in which R is lower alkyl. A is hydrogen, fluorine or chlorine, X is oxygen or sulfur, Y is hydrogen, fluorine, chlorine, or bromine, and Z is methyl or amino.

It has now been found that compounds of the following formula are active herbicides:

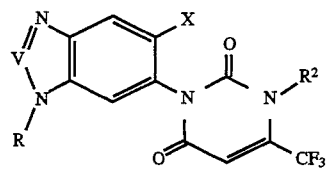

in which R is hydrogen, straight or branched chain lower alkyl, lower alkenyl, lower alkynyl, lower hydroxyalkyl, lower alkoxyalkyl, arylalkyl, substituted arylalkyl, aryloxyalkyl, or alkoxycarbonylalkyl; V is N or C—$R^1$; $R^1$ is hydrogen, lower alkyl, lower haloalkyl, or cyano; $R^2$ is lower alkyl or amino; and X is hydrogen or halogen, with the proviso that lower means having not more than six carbon atoms.

Preferred are those compounds in which $R^2$ is methyl or amino, X is hydrogen or fluoro, lower means having not more than four carbon atoms, and aryl is phenyl.

The compounds of the present invention were prepared by a variety of methods known to one skilled in the art, as illustrated in the following schemata.

In the method of Schema I, a 2-fluoro-5-(optionally substituted)-nitro-benzene was reacted with an appropriately substituted amine, for example, 2-propynylamine, under basic conditions, affording the corresponding N-substituted-4-optionally substituted-2-nitroaniline (1), for example, N-(2-propyn-1-yl)-4-fluoro-2-nitroaniline. Intermediate (1) was in turn reduced with either iron powder and acetic acid in ethyl acetate or with tin(II) chloride dihydrate and sodium borohydride in ethanol, yielding the corresponding 2-(substituted amino)-5-optionally substituted aniline (2), for example, 2-(2-propyn-1-ylamino)-5-fluoroaniline. The so-prepared aniline (2) was then cyclized with either trifluoroacetic acid (when $R^1$ is —$CF_3$) or acetic acid (when $R^1$ is —$CH_3$), affording the corresponding 1-substituted-2-(methyl or trifluoromethyl)-5-optionally substituted benzimidazole (3), for example, 1-(2-propyn-1-yl)-2-trifluoromethyl-5-fluorobenzimidazole. Nitration of the benzimidazole (3) with 70% nitric acid in concentrated sulfuric acid yielded an isomeric mixture of 1,2-disubstituted-4-nitro-5-optionally substituted benzimidazole (4A) and 1,2-disubstituted-5-optionally substituted-6-nitrobenzimidazole (4B). The nitrobenzimidazole isomers (4A) and (4B) were separated by column chromatography, and isomer (4B), for example, 2-propyn-1-yl-2-trifluoromethyl-5-fluoro-6-nitrobenzimidazole, was reduced with iron powder in ethyl acetate and acetic acid, affording the corresponding 1,2-disubstituted-5-optionally substituted-6-aminobenzimidazole (5). Intermediate (5) was then treated with ethyl chloroformate in pyridine, yielding the corresponding 1,2-disubstituted-5-optionally substituted-6-ethoxycarbonylaminobenzimidazole [generic structure (6), where V is C—$R^1$]. The 6-substituted-aminobenzimidazole (6) was, in turn, cyclized with ethyl 3-amino-4,4,4-trifluoro-2-butenoate and sodium methoxide in the presence of DBU in N,N-dimethylformamide, affording the corresponding 3-(1,2-disubstituted)-5-optionally substituted benzimidazol-6-yl)-6-trifluoromethyluracil (7). The intermediate uracil (7) was in turn alkylated with an appropriate alkyl halide and potassium carbonate in acetone, yielding the desired 1-alkyl-3-(1,2-disubstituted-5-optionally substituted benzimidazol-6-yl)-6-trifluoromethyluracil (II), for example, 1-methyl-3-[1-(propyn-2-yl)-2-trifluoromethyl-5-fluorobenzimidazol-6-yl]6-trifluoromethyluracil (Compound 12). Example 1 provides a detailed description of how these reactions were conducted.

In Schema 2, a 2-(optionally substituted)-5-haloaniline, for example, 2,5-difluoroaniline, was reacted with para-toluenesulfonyl chloride in pyridine, yielding the corresponding N-(4-methylphenylsulfonyl)-2-(optionally substituted)-5-haloaniline (8). The protected aniline intermediate (8) was in turn nitrated with 90% nitric acid in the presence of sodium nitrite in water and acetic acid, affording the N-(4-methylphenylsulfonyl)-2-(optionally substituted)-5-halo-4-nitroaniline (9), for example, N-(4-methylphenylsulfonyl)-2,5-difluoro-4-nitroaniline. The so-prepared nitroaniline (9) was then treated with concentrated sulfuric acid in water, yielding the corresponding 2-(optionally substituted)-5-halo-4-nitroaniline (10), for example, 2,5-difluoro-4-nitroaniline. The appropriate 4-nitroaniline (10) was then treated with ethyl chloroformate in pyridine, a method previously described, or sodium hydride and sodium hydroxide in ethanol and N,N-dimethylformamide, yielding the corresponding N-ethoxycarbonyl-2-(optionally substituted)-5-halo-4-nitroaniline (11). The so-prepared intermediate (11) was then treated with an appropriately substituted amine, for example, 2-methylpropylamine, under basic conditions, a method previously described, yielding the corresponding N-(substituted)-3-ethoxycarbonylamino-4-(optionally substituted)-6-nitroaniline (12). Reduction of the 6-nitroaniline (12)with iron powder, hydrochloric acid, and acetic acid in ethanol, or by hydrogenation in the presence of platinum oxide in ethanol, afforded the corresponding 2-(substituted amino)-4-ethoxycarbonylamino-5-(optionally substituted)aniline (13), for example, 2-(2-methylpropylamino)-4-ethoxycarbonylamino-5-fluoroaniline. Example 2 provides a detailed description of how the reactions to obtain (8)–(13) were conducted.

At this point the aniline (13), was either converted to intermediate benzimidazoles [generic structure (6), where V is C—$R^1$] or benzotriazoles [generic structure (6), where V is N].

To prepare the intermediate benzotriazoles (6), the aniline (13), for example, 2-(2-propen-1-ylamino)-4-ethoxycarbonylamino-5-fluoroaniline, was cyclized with sodium nitrite in aqueous dilute sulfuric acid, affording the corresponding 1-substituted-5-optionally substituted-6-ethoxycarbonylaminobenzotriazole (6). The intermediate benzotriazole (6) was in turn converted to the corresponding intermediate (7) and the desired 1-alkyl-3-(1-substituted-5-optionally substituted benzotriazol-6-yl)-6-trifluoromethyluracils (II), for example, 1-methyl-3-[1-(2-propen-1-yl)-5-fluorobenzotriazol-6-yl]-6-trifluoromethyluracil (Compound 18), by methods described above. Example 6 provides a detailed description of how the reactions to prepare the benzotriazolyl substituted uracils (II) were conducted.

In many cases the intermediate benzimidazole (6) was prepared directly by the cyclization of the aniline (13), for example, 2-(2-methylpropylamino)-4-ethoxycarbonylamino-5-fluoroaniline, with trifluoroacetic acid (where $R^1$ is —$CF_3$) in toluene (Step G of Example 2), or the aniline (13), for example, 2-propylamino-4-ethoxycarbonylamino-5-fluoroaniline, with formic acid (where $R^1$ is hydrogen). However, depending on the substituents R and X on the aniline (13), this reaction did not always proceed directly to the intermediate benzimidazole (6). For example, when 2-(3-chlorophenylmethylamino)-4-ethoxycarbonylamino-5-fluoroaniline (R is 3-chlorophenylmethyl, X is fluoro) (13) was treated with trifluoroacetic acid in toluene as described above (Step C of Example 3), the uncyclized intermediate N-trifluoromethylcarbonyl-2-[(trifluoromethylcarbonyl)(3-chlorophenylmethyl)amino]-4-ethoxycarbonylamino-5-fluoroaniline (14)was obtained. The intermediate (14) was then treated with potassium carbonate and water in methanol to obtain the aniline, 2-[(trifluoromethylcarbonyl)(3-chlorophenylmethyl)amino]-4-ethoxycarbonylamino-5-fluoroaniline (15). The aniline (15) was in turn heated in toluene, affording the intermediate benzimidazole (6).

In yet another example, when 2-(2-methylpropylamino)-4-(ethoxycarbonylamino)aniline (R is 2-methylpropyl, X is hydrogen) (13) was treated with trifluoroacetic acid in toluene as described above (Step D of Example 7), a 1:1 mixture of the intermediate 1-(2-methylpropyl)-2-trifluoromethyl-6-ethoxycarbonylaminobenzimidazole (6), and the uncylized intermediate, N-trifluoromethylcarbonyl-2-[(trifluoromethylcarbonyl)(2-methylpropyl)amino]-4-(ethoxycarbonylamino)aniline (14) was obtained. Treatment of the mixture of the intermediate benzimidazole (6) and (14) with potassium carbonate and water in methanol resulted in the direct conversion of intermediate (14) to the intermediate benzimidazole (6).

The intermediate benzimidazole (6), regardless of how it was obtained, was in turn converted to the corresponding intermediate (7) and the desired 1-alkyl-3-(1-substituted-5-optionally substituted benzimidazol-6-yl)-6-trifluoromethyluracils (II), by methods described above. Examples 2, 3, 6 and 7 provide detailed descriptions of how these reactions were conducted.

Certain compounds of the present invention may exist as tautomeric mixtures. Compound 1 (I) is an inseparable tautomeric mixture. The chemistry outlined in Schema 3 depicts a method by which Compound 1, and the like, and compounds derived therefrom, may be prepared. A 2-optionally substituted-4-nitrophenyl isocyanate was cyclized with ethyl 4,4,4-trifluoro-2-butenoate and sodium methoxide in the presence of DBU in N,N-dimethylformamide, affording the corresponding 3-(2-optionally substituted-4-nitrophenyl)-6-trifluoromethyluracil (16). The uracil (16) was in turn alkylated with alkyl iodide and potassium carbonate in acetone, yielding the corresponding 1-alkyl-3-(2-optionally substituted-4-nitrophenyl)-6-trifluoromethyluracil (17). The uracil (17) was then reduced with iron powder, hydrochloric acid, and acetic acid in ethanol, affording the 1-alkyl-3-(2-optionally substituted-4-aminophenyl)-6-trifluoromethyluracil (18), which was in turn reacted with trifluoroacetic anhydride in trifluoroacetic acid, to yield the corresponding 1-alkyl-3-[2-optionally substituted-4-(trifluoromethylcarbonylamino)phenyl]-6-trifluoromethyluracil (19). Intermediate uracil (19) was then nitrated with 70% nitric acid in concentrated sulfuric acid, yielding the appropriately nitrated uracil (20), for example, 1-methyl-3-[3-nitro-4-(trifluoromethylcarbonylamino) phenyl]-6-trifluoromethyluracil. Reduction of the uracil (20) with iron powder, hydrochloric acid, and acetic acid in ethanol, yielded directly the tautomeric mixture (I), for example, the mixture of 1-methyl-3-(2-trifluoromethylbenzimidazol-5-yl)-6-trifluoromethyluracil and 1-methyl-3-(2-trifluoromethylbenzimidazol-6-yl)-6-trifluoromethyluracil (Compound 1). Example 4 provides detailed descriptions of how these reactions were conducted.

The tautomeric mixture of 1-methyl-3-(2-trifluoromethylbenzimidazol-5-yl)-6-trifluoromethyluracil and 1-methyl-3-(2-trifluoromethylbenzimidazol-6-yl)-6-trifluoromethyluracil (Compound 1) prepared above was further reacted with an appropriately substituted halide, for example, 3-bromopropene, and sodium carbonate in N,N-dimethylformamide, yielding a mixture of 1-methyl-3-[1-(2-propen-1-yl)-2-trifluoromethylbenzimidazol-6-yl]-6-trifluoromethyluracil (II) (Compound 9) and 1-methyl-3-[1-(2-propen-1-yl)-2-trifluoromethylbenzimidazol- 5-yl]-6-trifluoromethyluracil (III) (Compound 10). The mixture of (II) and (III) was separated by high pressure liquid chromatography. Example 5 describes how these reactions were conducted.

In Schema 4, a 1-alkyl-3-(1-alkoxyalkyl-2-substituted-5-optionally substituted benzimidazol-6-yl)-6-trifluoromethyluracil (II) or a 1-alkyl-3-(1-alkoxyalkyl-5-optionally substituted benzotriazol-6-yl)-6-trifluoromethyluracil (II) was treated with boron tribromide in methylene chloride, yielding the corresponding alcohol, for example, 2-[2-trifluoromethyl-5-fluoro-6-(1-methyl-6-trifluoromethyluracil-3-yl)benzimidazol-1-yl]propan-1-ol (II-1). The alcohol was then oxidized with chromic acid in acetone, affording the corresponding acid, for example, 2-[2-trifluoromethyl-5-fluoro-6-(1-methyl-6-trifluoromethyluracil-3-yl)benzimidazol-1-yl]propanoic acid (II-2). The acid was in turn esterified with an appropriate alcohol, for example, 1-methylethanol, sulfuric acid, and molecular sieves, yielding the desired ester, for example, 1-methylethyl 2-[2-trifluoromethyl-5-fluoro-6-(1-methyl-6-trifluoromethyluracil-3-yl)-benzimidazol-1-yl] propanoate (II-3).

In Schema 5, the propan-1-ol (II-1) was treated with thionyl chloride under basic conditions in diethyl ether, affording the desired 1-alkyl-3-(1-haloalkyl-2-substituted-5-optionally substituted benzimidazol-6-yl)-6-trifluoromethyluracil (II-4), for example, 1-methyl-3-[1-(1-methyl-2-chloroethyl)-2-trifluoromethyl-5-fluorobenzimidazol-6-yl]-6-trifluoromethyluracil.

Also in Schema 5, the propanoic acid (II-2) was reacted with an appropriately substituted amine, for example, N-(phenylmethyl)amine, 1-hydroxybenzothiazole, and 1-(3-dimethylaminopropyl)-3-ethylcarbodiimide hydrochloride in methylene chloride, affording the desired amide, for example, N-phenylmethyl-2-[2-trifluoromethyl-5-fluoro-6-(1-methyl-6-trifluoromethyluracil-3-yl)benzimidazol-1-yl] propanecarboxamide (II-5).

The chemistry described in Schema 4 and 5 will also provide the corresponding benzotriazolyl uracil derivatives.

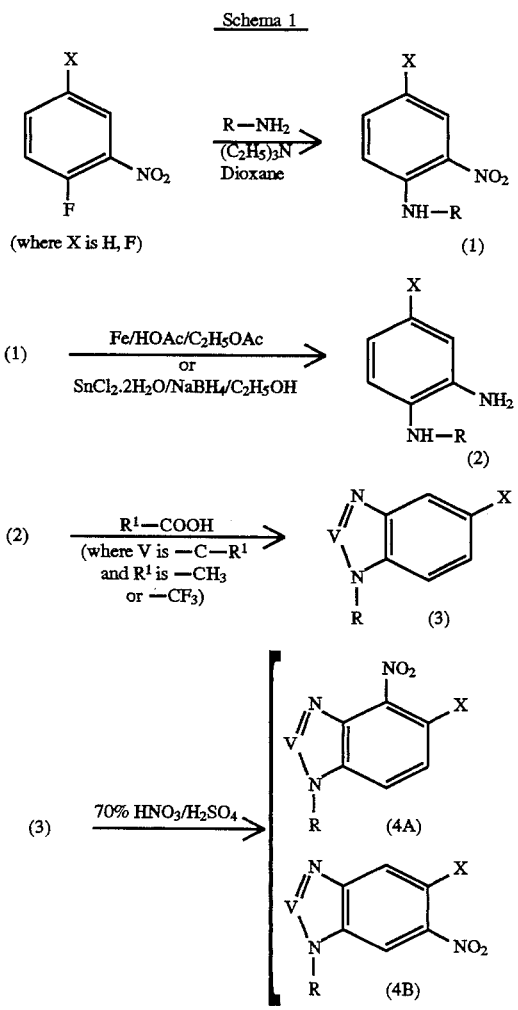

Schema 1 -continued
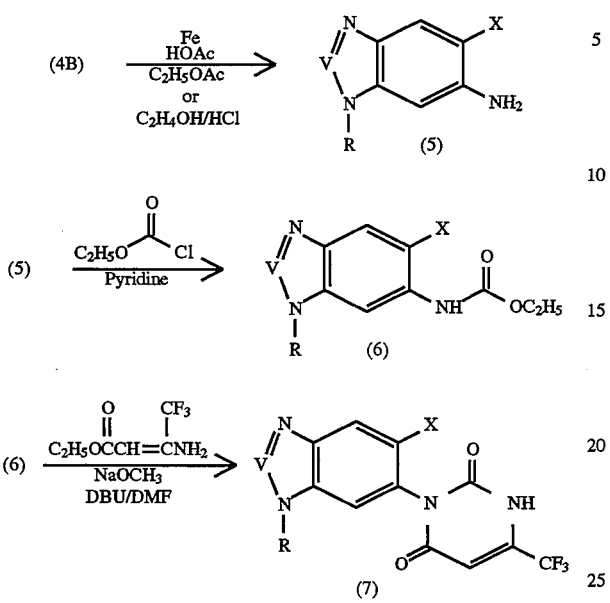
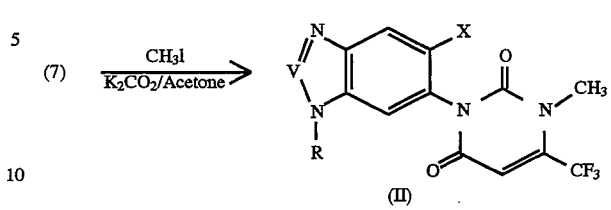
Schema 2
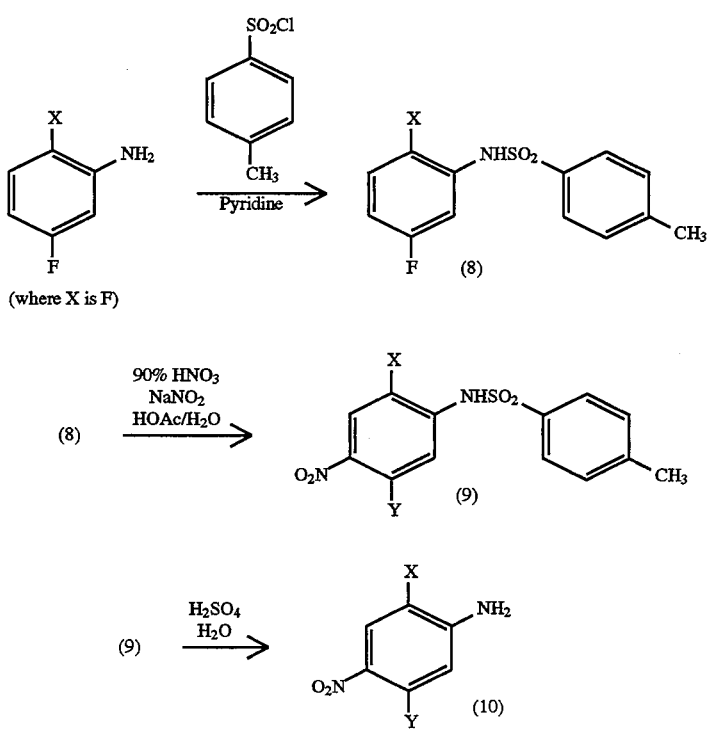
(where Y is Cl, F; when Y is Cl, intermediate (10) is commercially available)

-continued
Schema 2
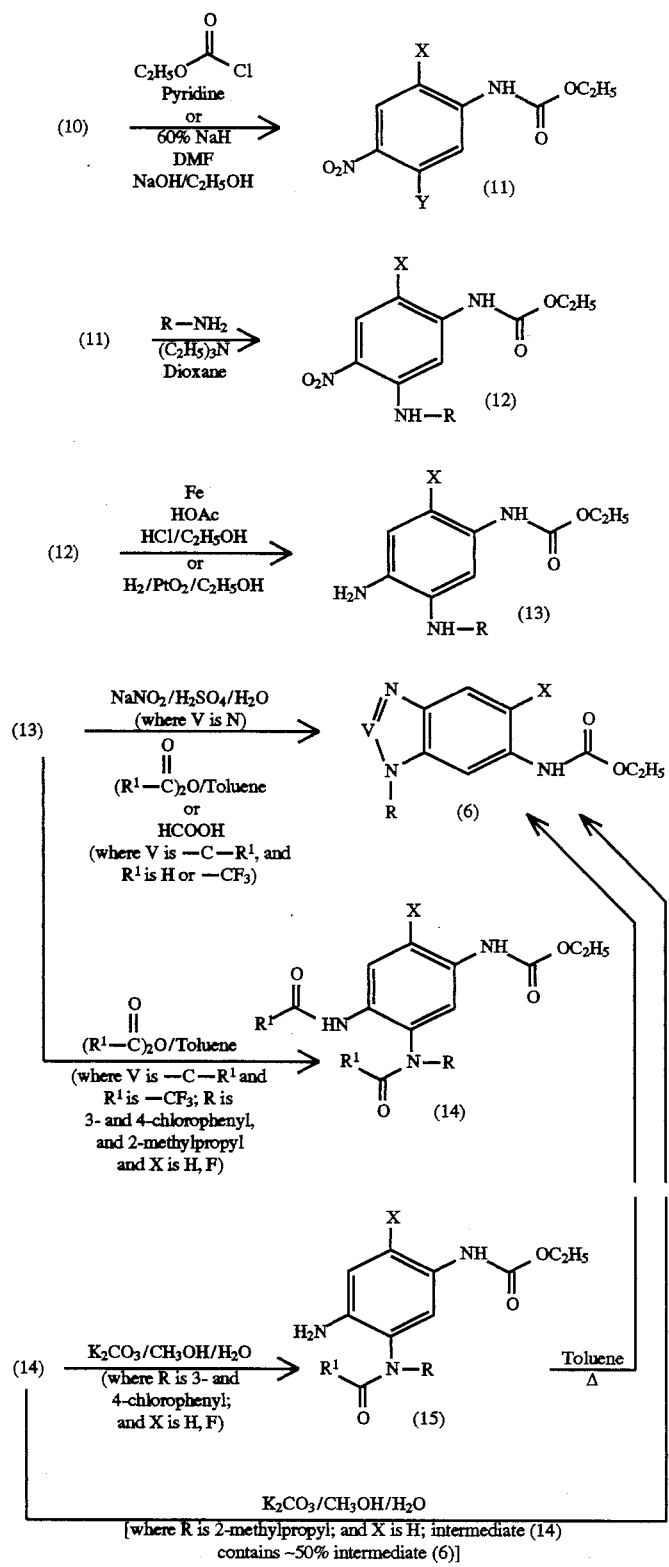

-continued
Schema 2
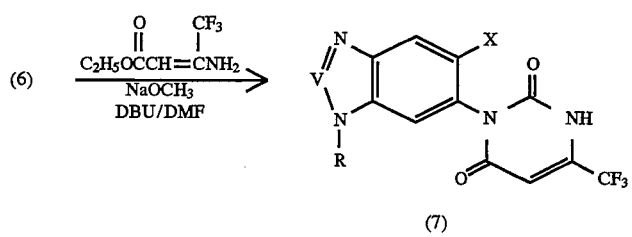
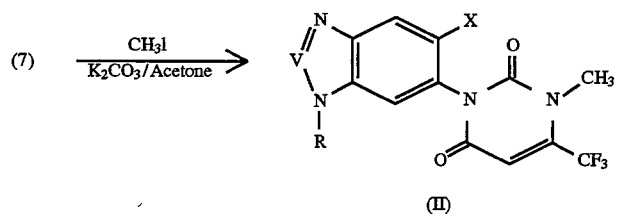
Schema 3
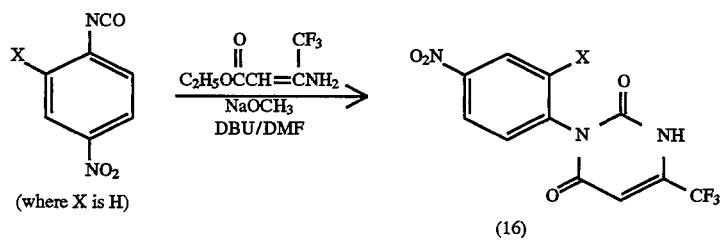
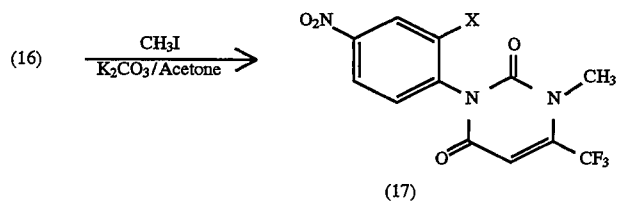
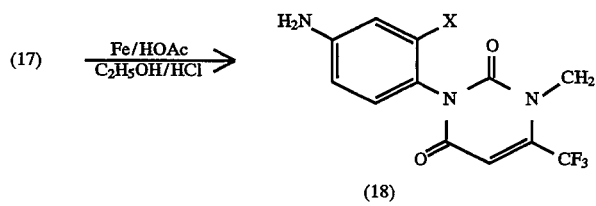
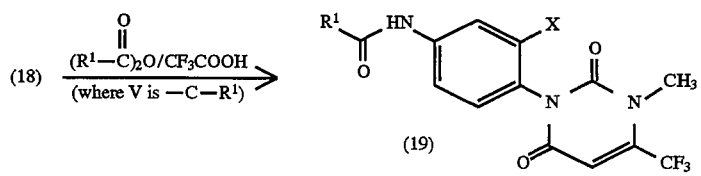
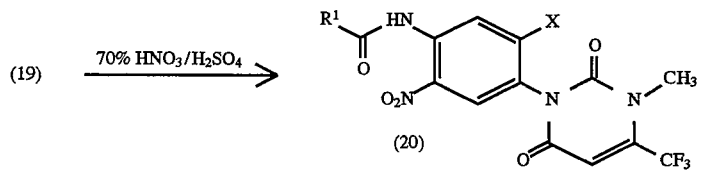

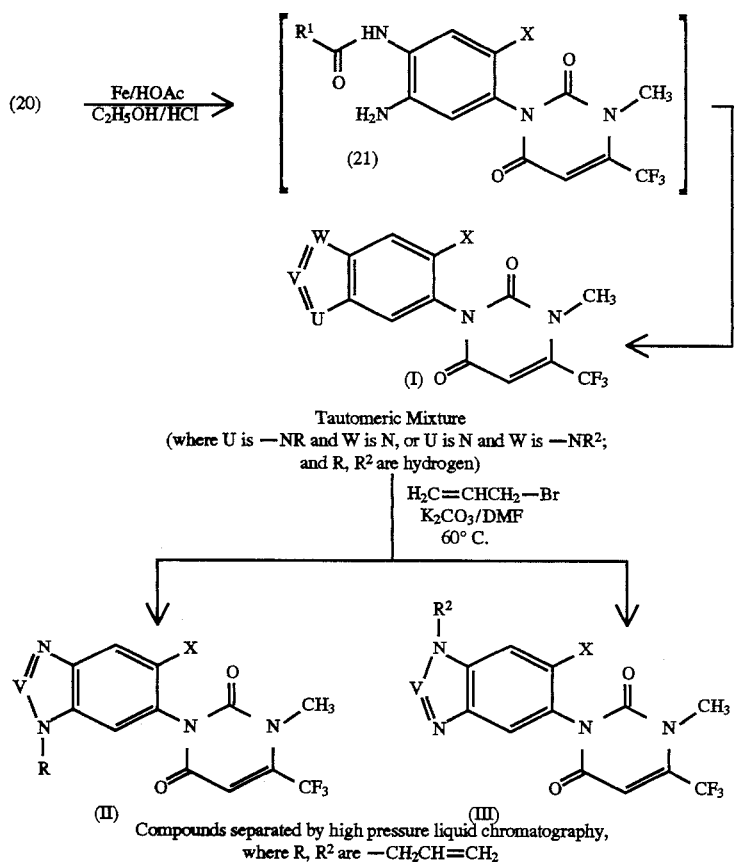
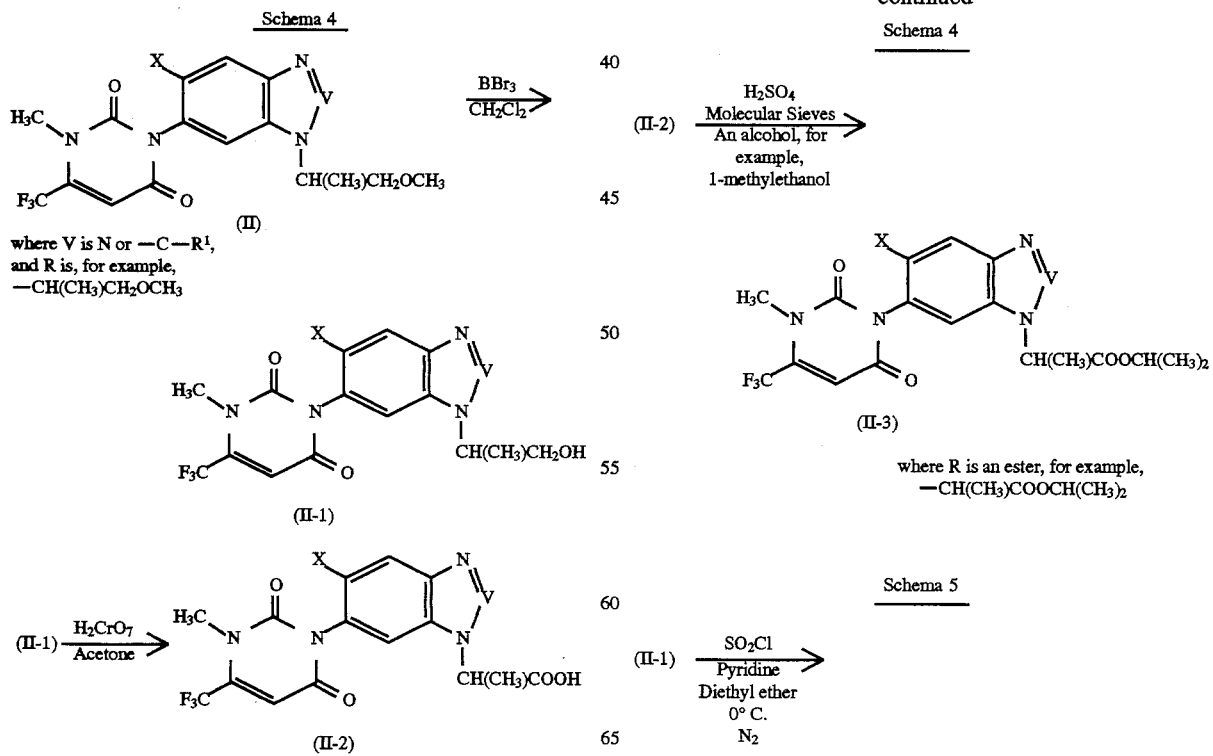

-continued
Schema 5

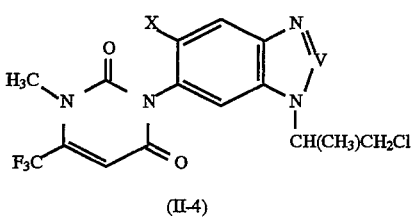

(II-4)

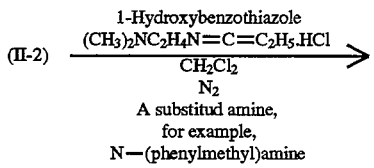

1-Hydroxybenzothiazole
(CH$_3$)$_2$NC$_2$H$_4$N=C=C$_2$H$_5$·HCl
———————————————→
CH$_2$Cl$_2$
N$_2$ A substitud amine,
for example,
N—(phenylmethyl)amine

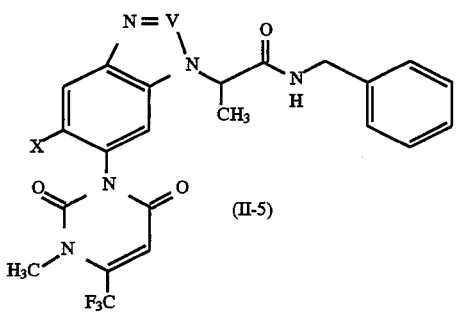

(II-5)

where R is a carboxamide, for example,

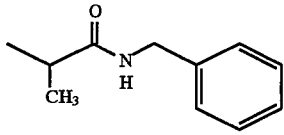

The following examples give more detailed descriptions of the manner in which the compounds of the invention were prepared.

EXAMPLE 1

SYNTHESIS OF 1-METHYL-3-[1-(2-PROPYN-1-YL)-2-TRIFLUOROMETHYL-5-FLUOROBENZIMIDAZOL-6-YL]-6-TRIFLUOROMETHYLURACIL (COMPOUND 11)

Step A Synthesis of N-(2-propyn-1-yl)-4-fluoro-2-nitroaniline as an intermediate To a stirred solution of 15.0 grams (0.094 mole) of 2,5-difluoronitrobenzene in 250 mL of dioxane was added 100 mL of triethylamine, followed by 7.3 grams (0.132 mole) of 2-propyn-1-ylamine. The reaction mixture was then warmed to reflux, where it was stirred for about four hours, then cooled to ambient temperature and poured into cold water. The resultant solid precipitate was collected by filtration and dried, yielding 10.0 grams of N-(2-propyn-1-yl)-4-fluoro-2-nitroaniline. The NMR spectrum was consistent with the proposed structure.

Step B Synthesis of 2-(2-propyn-1-ylamino)-5-fluoroaniline as an intermediate

Under a nitrogen atmosphere, 5.0 grams (0.026 mole) of N-(2-propyn-1-yl)-4-fluoro-2-nitroaniline in 250 mL of ethanol was added to 25.8 grams (0.114 mole) of stirred tin(II) chloride dihydrate. The reaction mixture was then warmed to 60° C. over a one hour period, after which 98% sodium borohydride pellets were added portionwise until thin layer chromatographic analysis of the reaction mixture indicated that the intermediate nitroaniline had been consumed. Consumption of the nitroaniline required about 2.0 grams (0.052 mole) of sodium borohydride. The reaction mixture was then cooled to about 10° C., and 50 mL of cold water, followed by 15 mL of cold aqueous 10% sodium hydroxide, was added dropwise. After this time, the reaction mixture was concentrated under reduced pressure to remove the majority of the ethanol solvent. The concentrate was extracted with four 75 mL portions of diethyl ether. The combined extracts were washed with aqueous 5% sodium hydroxide and then with an aqueous solution saturated with sodium chloride. The organic layer was dried over sodium sulfate and filtered. The filtrate was concentrated under reduced pressure to a residual oil, which was subjected to column chromatography on silica gel, with 1:3 ethyl acetate-:hexane as the eluant. The product-containing fractions were combined and concentrated under reduced pressure, yielding 5.0 grams of 2-(2-propyn-1-ylamino)-5-fluoroaniline. The NMR spectrum was consistent with the proposed structure.

Step C Synthesis of 1-(2-propyn-1-yl)-2-trifluoromethyl-5-fluorobenzimidazole as an intermediate Under a nitrogen atmosphere, a stirred solution of 5.0 grams (0.030 mole) of 2-propyn-1-ylamino)-5-fluoroaniline in 70 mL of trifluoroacetic acid was heated at reflux for 1.5 hours. The reaction mixture was then cooled to ambient temperature and poured into ice water. The mixture was extracted thoroughly with portions of diethyl ether. The combined extracts were washed with an aqueous solution saturated with sodium bicarbonate and then dried with magnesium sulfate. The mixture was filtered, and the filtrate concentrated under reduced pressure to a residual oil. The oil was triturated with cold water, and the resultant solid was collected by filtration. The solid was dried, yielding 5.0 grams of 1-(2-propyn-1-yl)-2-trifluoromethyl-5-fluorobenzimidazole. The NMR spectrum was consistent with the proposed structure. The reaction was repeated.

Step D Synthesis of a mixture of 1-(2-propyn-1-yl)-2-trifluoromethyl-5-fluoro-6-nitrobenzimidazole and 1-(2-propyn-1-yl)-2-trifluoromethyl-4-nitro-5-fluorobenzimidazole as intermediates Under a nitrogen atmosphere, a solution of 7.0 grams (0.028 mole) of 1-(2-propyn-1-yl)-2-trifluoromethyl-5-fluorobenzimidazole in 35 mL of concentrated sulfuric acid was stirred, and 3.3 grams (0.036 mole) of 70% nitric acid was added dropwise. During the addition the reaction caused the reaction mixture temperature to rise, at which time the reaction mixture was cooled to about 0° C. for the remainder of the addition. Upon completion of the addition, the reaction mixture was stirred at about 0° C. for one hour and then was allowed to warm to ambient temperature as it stirred for about 18 hours. The reaction mixture was poured into 300 mL of cold water, and the mixture was extracted thoroughly with ethyl acetate. The combined extracts were washed with an aqueous solution saturated with sodium chloride. The organic layer was dried with magnesium sulfate and filtered. The filtrate was concentrated under reduced pressure to a residue, which was subjected to column chromatography on silica gel, with 1:3 ethyl acetate:hexane as the eluant. The fractions containing 1-(2-propyn-1-yl)-2-trifluoromethyl-5-fluoro-6-nitrobenzimidazole were combined and concentrated under reduced pressure, yielding 1.5 grams of that product. The NMR spectrum was consistent with the proposed structure.

Step E Synthesis of 1-(2-propyn-1-yl)-2-trifluoromethyl-5-fluoro-6-aminobenzimidazole as an intermediate A stirred mixture of 1.5 grams (0.005 mole) of 1-(2-propyn-1-yl)-2-trifluoromethyl-5-fluoro-6- nitrobenzimidazole, 1.0 gram (0.018 mole) of iron powder, and 10 mL of ethyl acetate in 35 mL of acetic acid was heated at 60° C. for two hours. The reaction mixture was then poured into water, and the mixture was extracted thoroughly with portions of ethyl acetate. The combined extracts were washed with aqueous solutions saturated with sodium bicarbonate and sodium chloride. The organic layer was dried with sodium sulfate and filtered. The filtrate was concentrated under reduced pressure to a residual oil, which was triturated with water, and the resultant solid collected by filtration. The solid was dried, yielding 1.3 grams of 1-(2-propyn-1-yl)-2-trifluoromethyl-5-fluoro-6-aminobenzimidazole. The NMR spectrum was consistent with the proposed structure.

Step F Synthesis of 1-(2-propyn-1-yl)-2-trifluoromethyl-5-fluoro-6-ethoxycarbonylaminobenzimidazole as an intermediate Under a nitrogen atmosphere, a stirred solution of 1.3 grams (0.005 mole) of 1-(2-propyn-1-yl)-2-trifluoromethyl-5-fluoro-6-aminobenzimidazole and 30 mL of pyridine was cooled to 0°–5° C., and 1.0 mL (0.011 mole) of ethyl chloroformate was added dropwise. Upon completion of the addition, the reaction mixture was allowed to warm to ambient temperature, where it stirred for about 18 hours. The reaction mixture was then poured into cold aqueous 3N hydrochloric acid. The resultant solid was collected by filtration and dried, yielding 2.3 grams of 1-(propyn-2-yl)-2-trifluoromethyl-5-fluoro-6-ethoxycarbonylaminobenzimidazole. The NMR spectrum was consistent with the proposed structure.

Step G Synthesis of 3-[1-(2-propyn-1-yl)-2-trifluoromethyl-5-fluorobenzimidazol-6-yl]-6-trifluoromethyluracil as an intermediate Under a nitrogen atmosphere, a stirred solution of 0.4 gram (0.005 mole) of sodium methoxide in 5 mL of N,N-dimethylformamide was cooled to about 0°–5° C., and 1.8 grams (0.005 mole) of ethyl 3-amino-4,4,4-trifluoro-2-butenoate in 15 mL of N,N-dimethylformamide was added dropwise. Upon completion of the addition, the reaction mixture was allowed to warm to ambient temperature where it stirred for 30 minutes. After this time, the reaction mixture was again cooled, and a solution of 1.8 grams (0.005 mole) of 1-(2-propyn-1-yl)-2-trifluoromethyl-5-fluoro-6-ethoxycarbonylaminobenzimidazole in 20 mL of N,N-dimethylformamide was added dropwise. The reaction mixture was heated to 110° C., and 0.24 mL (catalyst) of 1,8-diazabicyclo[5.4.0]undec-7-ene (DBU) was added in one portion. Upon completion of the addition, the reaction mixture was heated to about 130° C., where it stirred for about 3.5 hours. The reaction mixture was then allowed to cool to ambient temperature as it stirred for about 72 hours, after which the reaction mixture was poured into ice-cold aqueous 3N hydrochloric acid. The resultant precipitate was collected by filtration and dried, yielding 0.6 gram of 3-[1-(2-propyn-1-yl)-2-trifluoromethyl-5-fluorobenzimidazol-6-yl]-6-trifluoromethyluracil. The NMR spectrum was consistent with the proposed structure.

Step H Synthesis of 1-methyl-3-[1-(2-propyn-1-yl)-2-trifluoromethyl-5-fluorobenzimidazol-6-yl]-6-trifluoromethyluracil (Compound 11)

A solution of 0.6 gram (0.001 mole) of 3-[1-(2-propyn-1-yl)-2-trifluoromethyl-5-fluorobenzimidazol-6-yl]-6-trifluoromethyluracil, 0.4 gram (0.003 mole) of potassium carbonate, and 0.17 mL (0.003 mole) of methyl iodide in 30 mL of acetone was stirred at ambient temperature for about 18 hours, after which the reaction mixture was concentrated under reduced pressure to a residue. The residue was taken up in diethyl ether and washed with an aqueous solution saturated with sodium chloride. The organic layer was dried with magnesium sulfate and filtered. The filtrate was concentrated under reduced pressure to an oily residue, which was subjected to column chromatography on silica gel. Elution was accomplished using 1:3 ethyl acetate:hexane as the eluant. The product-containing fractions were combined and concentrated under reduced pressure, yielding 0.3 gram of 1-methyl-3-[1-(2-propyn-1-yl)-2-trifluoromethyl-5-fluorobenzimidazol-6-yl]-6-trifluoromethyluracil, mp 104°–105° C. The NMR spectrum was consistent with the proposed structure.

EXAMPLE 2

SYNTHESIS OF 1-METHYL-3-[1-(2-METHYLPROPYL)-2-TRIFLUOROMETHYL-5-FLUOROBENZIMIDAZOL-6-YL]-6-TRIFLUOROMETHYLURACIL (COMPOUND 6)

Step A Synthesis of N-(4-methylphenylsulfonyl)-2,5-difluoroaniline as an intermediate A stirred solution of 10.0 grams (0.077 mole) of 2,5-difluoroaniline and 16.2 grams (0.085 mole) of 4-methylphenylsulfonyl chloride in 50 mL of pyridine was heated at reflux for about 2.5 hours. The reaction mixture was then cooled and poured into ice-cold aqueous 3N hydrochloric acid. The resultant solid was collected by filtration and dried, yielding 22.0 grams of N-(4-methylphenylsulfonyl)-2,5-difluoroaniline. The NMR spectrum was consistent with the proposed structure.

Step B Synthesis of N-(4-methylphenylsulfonyl)-2,5-difluoro-4-nitroaniline as an intermediate A stirred solution of 20 mL (0.427 mole) of 90% nitric acid (fuming) in 170 mL of water was cooled in an ice-water bath, and 22.0 grams (0.077 mole) of N-(4-methylphenylsulfonyl)-2,5-difluoroaniline was added. To this mixture was added 170 mL of acetic acid and then 0.5 gram (0.008 mole) of sodium nitrite. Upon completion of the addition, the reaction mixture was warmed to 90° C., where it stirred for about 2.5 hours. The reaction mixture was then cooled and poured into cold water. The resultant precipitate was collected by filtration and dried, yielding about 25 grams of N-(4-methylphenylsulfonyl)-2,5-difluoro-4-nitroaniline. The NMR spectrum was consistent with the proposed structure.

Step C Synthesis of 2,5-difluoro-4-nitroaniline as an intermediate

A stirred solution of 25.0 grams (0.076 mole) of N-(4-methylphenylsulfonyl)-2,5-difluoro-4-nitroaniline in 50 mL of water was cooled in an ice-water bath, and 150 mL of concentrated sulfuric acid was carefully added portionwise. Upon completion of the addition, the reaction mixture was heated to about 90° C., where it stirred for about four hours. The reaction mixture was then cooled and poured into wet ice. The resultant solid was collected by filtration and dried, yielding about 19.0 grams of 2,5-difluoro-4-nitroaniline. The NMR spectrum was consistent with the proposed structure.

Step D Synthesis of N-ethoxycarbonyl-2,5-difluoro-4-nitroaniline as an intermediate Under a nitrogen atmosphere, a stirred mixture of 2.2 grams (0.055 mole) of sodium hydride (60% in mineral oil) in about 40 mL of N,N-dimethylformamide was cooled in an ice-bath, and a solution of 8.0 grams (0.046 mole) of 2,5-difluoro-4-nitroaniline in 100 mL of N,N-dimethylformamide was added dropwise. After the evolution of hydrogen ceased, 7.5 grams (0.069 mole) of ethyl chloroformate was added in small portions. Upon completion of the addition, the reaction mixture was allowed to warm to ambient temperature, where it stirred for about 20 hours. After this time, the reaction mixture was poured into aqueous 3N hydrochloric acid and ice. The resultant precipitate was collected by filtration and dissolved in ethanol. To this stirred solution was then added dropwise a solution of 3.3 grams (0.083 mole) of sodium hydroxide dissolved in a minimum of water. Upon completion of the addition, the reaction mixture was stirred at ambient temperature for about 25 minutes and then made acidic with concentrated hydrochloric acid. The reaction mixture was poured into water, and the resultant solid was collected by filtration. The solid was dried, yielding 7.0 grams of N-ethoxycarbonyl-2,5-difluoro-4-nitroaniline. The NMR spectrum was consistent with the proposed structure.

Step E Synthesis of N-(2-methylpropyl)-3-ethoxycarbonylamino-4-fluoro-6-nitroaniline as an intermediate This compound was prepared in a manner analogous to that of Step A of Example 1, using 3.0 grams (0.012 mole) of N-ethoxycarbonyl-2,5-difluoro-4-nitroaniline, 1.3 grams (0.018 mole) of 2-methylpropylamine, and 20 mL of triethylamine in 100 mL of dioxane. The yield of N-(2-methylpropyl)-3-ethoxycarbonylamino-4-fluoro-6-nitroaniline was 3.0 grams, mp 113°–114° C. The NMR spectrum was consistent with the proposed structure.

Step F Synthesis of 2-(2-methylpropylamino)-4-ethoxycarbonylamino-5-fluoroaniline as an intermediate A stirred mixture of 2.7 grams (0.009 mole) of N-(2-methylpropyl)-3-ethoxycarbonylamino-4-fluoro-6-nitroaniline, 2.0 grams (0.036 mole) of iron powder, 15 mL of acetic acid, and 0.5 mL (0.009 mole) of concentrated hydrochloric acid in 75 mL of ethanol was heated at reflux for about five hours. The reaction mixture was then concentrated under reduced pressure to a residue, which was taken up in ethyl acetate and washed with aqueous solutions saturated with sodium bicarbonate and sodium chloride. The organic layer was dried with sodium sulfate and filtered. The filtrate was concentrated under reduced pressure to a residue. NMR analysis of the residue indicated the presence of product and acetic acid. The residue was washed with several portions of an aqueous solution saturated with sodium bicarbonate, and then was extracted thoroughly with ethyl acetate. The combined extracts were dried with sodium sulfate and filtered. The filtrate was concentrated under reduced pressure, yielding 2.0 grams of 2-(2-methylpropylamino)-4-ethoxycarbonylamino-5-fluoroaniline.

Step G Synthesis of 1-(2-methylpropyl)-2-trifluoromethyl-5-fluoro-6-ethoxycarbonylaminobenzimidazole as an intermediate A stirred solution of 2.0 grams (0.008 mole) of 2-(2-methylpropylamino)-4-ethoxycarbonylamino-5-fluoroaniline and 1.9 grams (0.009 mole) of trifluoroacetic anhydride in 75 mL of toluene was heated at 45° C. for about 3.5 hours. After this time the reaction mixture was allowed to cool to ambient temperature, as it stirred for about 18 hours. The reaction mixture was then concentrated under reduced pressure to a residue, which was subjected to column chromatography on silica gel, with 1:1 ethyl acetate and hexane as the eluant. The product-containing fractions were combined and concentrated under reduced pressure, yielding 1.7 grams of 1-(2-methylpropyl)-2-trifluoromethyl-5-fluoro-6-ethoxycarbonylaminobenzimidazole. The NMR spectrum was consistent with the proposed structure.

Step H Synthesis of 3-[1-(2-methylpropyl)-2-trifluoromethyl-5-fluorobenzimidazol-6-yl]-6-trifluoromethyluracil as an intermediate This compound was prepared in a manner analogous to that of Step G of Example 1, using 1.7 grams (0.005 mole) of 1-(2-methylpropyl)-2-trifluoromethyl- 5-fluoro-6-ethoxycarbonylaminobenzimidazole, 0.9 gram (0.005 mole) of ethyl 3-amino-4,4,4-trifluoro-2-butenoate, 0.3 gram (0.006 mole) of sodium methoxide, and 0.24 mL (catalyst) of 1,8-diazabicyclo[5.4.0]undec-7-ene (DBU) in 50 mL of N,N-dimethylformamide. The yield of 3-[1-(2-methylpropyl)-2-trifluoromethyl-5-fluorobenzimidazol-6-yl]-6-trifluoromethyluracil was about 0.8 gram. The NMR spectrum was consistent with the proposed structure.

Step I Synthesis of 1-methyl-3-[1-(2-methylpropyl)-2-trifluoromethyl-5-fluorobenzimidazol-6-yl]-6-trifluoromethyluracil (Compound 6)

This compound was prepared in a manner analogous to that of Step H of Example 1, using 0.8 gram (0.002 mole) of 3-[1-(2-methylpropyl)-2-trifluoromethyl-5-fluorobenzimidazol-6-yl]-6-trifluoromethyluracil, 0.5 gram (0.004 mole) of potassium carbonate, and 0.38 mL (0.004 mole) of methyl iodide in 30 mL of acetone. The yield of 1-methyl-3-[1-(2-methylpropyl)-2-trifluoromethyl-5-fluorobenzimidazol-6-yl]-6-trifluoromethyluracil was 0.4 gram, mp 169°–170° C. The NMR spectrum was consistent with the proposed structure.

EXAMPLE 3

SYNTHESIS OF 1-METHYL-3-[1-(3-CHLOROPHENYLMETHYL)-2-TRIFLUOROMETHYL-5-FLUOROBENZIMIDAZOL6-YL]-6-TRIFLUOROMETHYLURACIL (COMPOUND 14)

Step A Synthesis of N-(3-chlorophenylmethyl)-3-ethoxycarbonylamino-4-fluoro-6-nitroaniline as an intermediate This compound was prepared in a manner analogous to that of Step A of Example 1, using 4.1 grams (0.017 mole) of N-ethoxycarbonyl-2,5-difluoro-4-nitroaniline (prepared as in Steps A–D of Example 2), 3.5 grams (0.025 mole) of 3-chlorophenylmethylamine, and 20 mL of triethylamine in 100 mL of dioxane. The yield of N-(3-chlorophenylmethyl)-3-ethoxycarbonylamino-4-fluoro- 6-nitroaniline was 6.2 grams, mp 110°–112° C. The NMR spectrum was consistent with the proposed structure.

Step B Synthesis of 2-(3-chlorophenylmethylamino)-4-ethoxycarbonylamino-5-fluoroaniline as an intermediate This compound was prepared in a manner analogous to that of Step F of Example 2, using 5.8 grams (0.016 mole) of N-(3-chlorophenylmethyl)-3-ethoxycarbonylamino-4-fluoro-6-nitroaniline, 3.5 grams (0.063 mole) of iron powder, 25 mL of acetic acid, and 0.9 mL (0.016 mole) of concentrated hydrochloric acid in 150 mL of ethanol. The yield of 2-(3-chlorophenylmethylamino)-4-ethoxycarbonylamino-5-fluoroaniline was 4.6 grams. The NMR spectrum was consistent with the proposed structure.

Step C Synthesis of N-trifluoromethylcarbonyl-2-[(trifluoromethylcarbonyl)(3-chlorophenylmethyl)amino]-4-ethoxycarbonylamino-5-fluoroaniline as an intermediate This compound was prepared in a manner analogous to that of Step G of Example 2, using 4.6 grams (0.014 mole) of 2-(3-chlorophenylmethylamino)-4-ethoxycarbonylamino-5-fluoroaniline and 2.8 mL (0.020 mole) of trifluoroacetic anhydride in about 75 mL of toluene. The reaction product was subjected to column chromatography on silica gel, with 1:2 ethyl acetate in hexane as the eluant. The product-containing fractions were combined and concentrated under reduced pressure, yielding 3.7 grams of product. NMR and mass spectral analysis of the product indicated that it was not the intended 1-(3-chlorophenylmethyl)-2-trifluoromethyl-5-fluoro-6-ethoxycarbonylaminobenzimidazole intermediate, but rather an uncyclized intermediate, N-trifluoromethylcarbonyl-2-[(trifluoromethylcarbonyl)(3-chlorophenylmethyl)amino]-4-ethoxycarbonylamino-5-fluoroaniline.

Step D Synthesis of 2-[(trifluoromethylcarbonyl)(3-chlorophenylmethyl)amino]-4-ethoxycarbonylamino-5-fluoroaniline as an intermediate A solution of 3.7 grams (0.007 mole) of N-trifluoromethylcarbonyl-2-[(trifluoromethylcarbonyl)(3-chlorophenylmethyl)amino]-4-ethoxycarbonylamino-5-fluoroaniline in 50 mL of methanol was stirred, and a solution of 1.0 gram (0.007 mole) of potassium carbonate in a minimum amount of water was added. The reaction mixture was then heated at reflux for about three hours, after which the reaction mixture was cooled, poured into cold water, and acidified to a pH of 6 with aqueous 3N hydrochloric acid. The resultant solid was collected by filtration and dried, yielding 3.2 grams of 2-[(trifluoromethylcarbonyl)(3-chlorophenylmethyl)amino]-4-ethoxycarbonylamino-5-fluoroaniline. The NMR spectrum was consistent with the proposed structure.

Step E Synthesis of 1-(3-chlorophenylmethyl)-2-trifluoromethyl-5-fluoro-6-ethoxycarbonylaminobenzimidazole as an intermediate A stirred solution of 3.2 grams (0.007 mole) of 2-[(trifluoromethylcarbonyl)(3-chlorophenylmethyl)amino]-4-ethoxycarbonylamino-5-fluoroaniline in 100 mL of toluene was heated at reflux for about 4.5 hours. After this time, the reaction mixture was concentrated under reduced pressure to a residue, which was triturated with petroleum ether, and the resultant solid was collected by filtration, yielding 2.5 grams of 1-(3-chlorophenylmethyl)-2-trifluoromethyl-5-fluoro-6-ethoxycarbonylaminobenzimidazole, mp 144°–146° C. The NMR spectrum was consistent with the proposed structure.

Step F Synthesis of 3-[1-(3-chlorophenylmethyl)-2-trifluoromethyl-5-fluorobenzimidazol-6-yl]-6-trifluoromethyluracil as an intermediate This compound was prepared in a manner analogous to that of Step G of Example 1, using 2.0 grams (0.005 mole) of 1-(3-chlorophenylmethyl)-2-trifluoromethyl-5-fluoro-6-ethoxycarbonylaminobenzimidazole, 0.9 gram (0.005 mole) of ethyl 3-amino-4,4,4-trifluoro-2-butenoate, 0.3 gram (0.006 mole) of sodium methoxide, and 0.24 mL (catalyst) of 1,8-diazabicyclo-[5.4.0]undec-7-ene (DBU) in 50 mL of N,N-dimethylformamide. The yield of 3-[1-(3-chlorophenylmethyl)-2-trifluoromethyl-5-fluorobenzmidazol-6-yl]-6-trifluoromethyluracil was 1.9 grams, mp 134°–137° C. The NMR spectrum was consistent with the proposed structure.

Step G Synthesis of 1-methyl-3-[1-(3-chlorophenylmethyl)-2-trifluoromethyl-5-fluorobenzimidazol-6-yl]-6-trifluoromethyluracil (Compound 14)

This compound was prepared in a manner analogous to that of Step H of Example 1, using 1.2 grams (0.002 mole) of 3-[1-(3-chlorophenylmethyl)-2-trifluoromethyl-5-fluorobenzmidazol-6-yl]-6-trifluoromethyluracil, 0.7 gram (0.005 mole) of potassium carbonate, and 0.51 mL (0.005 mole) of methyl iodide in 40 mL of acetone. The yield of 1-methyl-3-[1-(3-chlorophenylmethyl)-2-trifluoromethyl-5-fluorobenzimidazol-6-yl]-6-trifluoromethyluracil was 0.7 gram, mp 91°–93° C. The NMR spectrum was consistent with the proposed structure.

EXAMPLE 4

SYNTHESIS OF A TAUTOMERIC MIXTURE OF 1-METHYL-3-(2-TRIFLUOROMETHYLBENZIMIDAZOL-5-YL)-6-TRIFLUOROMETHYLURACIL AND 1-METHYL-3-(2-TRIFLUOROMETHYLBENZIMIDAZOL-6-YL)-6-TRIFLUOROMETHYLURACIL (COMPOUND 1)

Step A Synthesis of 3-(4-nitrophenyl)-6-trifluoromethyluracil as an intermediate This compound was prepared in a manner analogous to that of Step G of Example 1, using 7.8 grams (0.048 mole) of 4-nitrophenyl isocyanate, 8.7 grams (0.048 mole) of ethyl 3-amino-4,4,4-trifluoro-2-butenoate, 3.1 grams (0.058 mole) of sodium methoxide, and 2.4 mL (catalyst) of 1,8-diazabicyclo-[5.4.0]undec-7-ene (DBU) in 120 mL of N,N-dimethylformamide. A 100% yield of 3-(4-nitrophenyl)-6-trifluoromethyluracil (14.5 grams) was assumed. This material was used in the following reaction without isolation.

Step B Synthesis of 1-methyl-3-(4-nitrophenyl)-6-trifluoromethyluracil as an intermediate To the stirred reaction mixture containing the crude 3-(4-nitrophenyl)-6-trifluoromethyluracil (14.5 grams—0.048 mole) from the preceding step was added 13.6 grams (0.096 mole) of methyl iodide and 3.3 grams (0.096 mole) of potassium carbonate. Upon completion of the addition, the reaction mixture was stirred at ambient temperature for about five hours, after which the reaction mixture was poured into water, and the resultant solid was collected by filtration. The solid was washed with petroleum ether and dried, yielding 13.0 grams of 1-methyl-3-(4-nitrophenyl)-6-trifluoromethyluracil. The NMR spectrum was consistent with the proposed structure.

Step C Synthesis of 1-methyl-3-(4-aminophenyl)-6-trifluoromethyluracil as an intermediate This compound was prepared in a manner analogous to that of Step F of Example 2, using 13.0 grams (0.041 mole) of 1-methyl-3-(4-nitrophenyl)-6-trifluoromethyluracil, 23.0 grams (0.410 mole) of iron powder, 2.3 mL (0.041 mole) of concentrated hydrochloric acid, and 40 mL of ethanol in 200 mL of acetic acid. The yield of 1-methyl-3-(4-aminophenyl)-6-trifluoromethyluracil was 6.6 grams. The NMR spectrum was consistent with the proposed structure.

Step D Synthesis of 1-methyl-3-[4-(trifluoromethylcarbonylamino)phenyl]-6-trifluoromethyluracil as an intermediate A stirred solution of 6.6 grams (0.023 mole) of 1-methyl-3-(4-aminophenyl)-6-trifluoromethyluracil in 100 mL of trifluoroacetic acid was cooled to 0°–5° C., and 5.3 grams (0.025 mole) of trifluoroacetic anhydride was added dropwise. Upon completion of the addition, the reaction mixture was stirred at ambient temperature for about two hours. After this time the reaction mixture was poured into ice water, and the resultant solid was collected by filtration. The solid was dried, yielding 5.8 grams of 1-methyl-3-[4-(trifluoromethylcarbonylamino)phenyl]-6-trifluoromethyluracil. The NMR spectrum was consistent with the proposed structure.

Step E Synthesis of 1-methyl-3-[3-nitro-4-(trifluoromethylcarbonylamino)phenyl]-6-trifluoromethyluracil as an intermediate This compound was prepared in a manner analogous to that of Step D of Example 1, using 5.8 grams (0.015 mole) of 1-methyl-3-[4-(trifluoromethylcarbonylamino)phenyl]-6- trifluoromethyluracil and 1.1 mL (0.017 mole) of 70% nitric acid in 60 mL of concentrated sulfuric acid. The yield of 1-methyl-3-[3-nitro-4-(trifluoromethylcarbonylamino) phenyl]-6-trifluoromethyluracil was 3.0 grams. The NMR spectrum was consistent with the proposed structure.

Step F Synthesis of a tautomeric mixture of 1-methyl-3-(2-trifluoromethylbenzimidazol-5-yl)-6-trifluoromethyluracil and 1-methyl-3-(2-trifluoromethylbenzimidazol-6-yl)-6-trifluoromethyluracil (Compound 1)

This compound was prepared in a manner analogous to that of Step F of Example 2, using 3.0 grams (0.007 mole) of 1-methyl-3-[3-nitro-4-(trifluoromethylcarbonylamino) phenyl]-6-trifluoromethyluracil, 2.3 grams (0.042 mole) of iron powder, 30 mL of acetic acid, and 0.6 mL (0.007 mole) of concentrated hydrochloric acid in 100 mL of ethanol. The product was an inseparable tautomeric 1:1 mixture of 1-methyl-3-(2-trifluoromethylbenzimidazol-5-yl)-6-trifluoromethyluracil and 1-methyl-3-(2-trifluoromethylbenzimidazol-6-yl)-6-trifluoromethyluracil. The yield was about 1.8 grams, mp>200° C. The NMR spectrum was consistent with the proposed structures.

EXAMPLE 5

SYNTHESIS OF 1-METHYL-3-[1-(2-PROPEN-1-YL)-2-TRIFLUOROMETHYLBENZIMIDAZOL-5-YL]-6-TRIFLUOROMETHYLURACIL AND 1-METHYL- 3-[1-(2-PROPEN-1-YL)-2-TRIFLUOROMETHYLBENZIMIDAZOL-6-YL]-6-TRIFLUOROMETHYLURACIL (COMPOUND 9)

Under a nitrogen atmosphere, 1.3 grams (0.003 mole) of a tautomeric mixture of 1-methyl-3-(2-trifluoromethylbenzimidazol-5-yl)-6-trifluoromethyluracil and 1-methyl-3-(2-trifluoromethylbenzimidazol-6-yl)-6-trifluoromethyluracil (prepared in Example 4) in 15 mL of N,N-dimethylformamide was stirred, and 0.9 gram (0.007 mole) of potassium carbonate was added. The reaction mixture was then stirred at ambient temperature for one hour, and 0.5 gram (0.004 mole) of 3-bromopropene was added in one portion. Upon completion of the addition, the reaction mixture was stirred at ambient temperature for an additional two hours. The reaction mixture was then poured into water, and the resultant solid precipitate was collected by filtration. The solid was washed with water and then with diethyl ether. Thin layer chromatographic analysis of the solid indicated it to be a 1:1 mixture of the proposed products. The solid was subjected to high pressure liquid chromatography, with 5% 1-methylethanol in hexane as the eluant. The appropriate product-containing fractions were combined and concentrated under reduced pressure, yielding 0.3 gram of 1-methyl-3-[1-(2-propen-1-yl)-2-trifluoromethylbenzimidazol-6-yl]-6-trifluoromethyluracil, mp 171°–173° C. (compound 9). Other appropriate product-containing fractions were combined and concentrated under reduced pressure, yielding 0.4 gram of 1-methyl-3-[1-(2-propen-1-yl)-2-trifluoromethylbenzimidazol-5-yl]-6-trifluoromethyluracil, mp 185°–187° C. The NMR spectra were consistent with the proposed structures.

EXAMPLE 6

SYNTHESIS OF 1-METHYL-3-[1-(2-PROPEN-1-YL)-5-FLUOROBENZOTRIAZOL-6-YL]-6-TRIFLUOROMETHYLURACIL (COMPOUND 24)

Step A Synthesis of N-(2-propen-1-yl)-3-ethoxycarbonylamino-4-fluoro-6-nitroaniline as an intermediate This compound was prepared in a manner analogous to that of Step A of Example 1, using 4.6 grams (0.019 mole) of N-ethoxycarbonyl-2,5-difluoro-4-nitroaniline (prepared as in Steps A–D of Example 2), 1.6 grams (0.028 mole) of allylamine, and 21 mL of triethylamine in 120 mL of dioxane. The yield of N-(2-propen-1-yl)-3-ethoxycarbonylamino-4-fluoro-6-nitroaniline was 4.8 grams. The NMR spectrum was consistent with the proposed structure.

Step B Synthesis of 2-(2-propen-1-ylamino)-4-ethoxycarbonylamino-5-fluoroaniline as an intermediate This compound was prepared in a manner analogous to that of Step F of Example 2, using 4.8 grams (0.017 mole) of N-(2-propen-1-yl)-3-ethoxycarbonylamino-4-fluoro-6-nitroaniline, 3.8 grams (0.068 mole) of iron powder, 20 mL of acetic acid, and 1.0 mL (0.019 mole) of concentrated hydrochloric acid in 100 mL of ethanol. The yield of 2-(2-propen-1-ylamino)-4-ethoxycarbonylamino-5-fluoroaniline was 4.7 grams. The NMR spectrum was consistent with the proposed structure.

Step C Synthesis of 1-(2-propen-1-yl)-5-fluoro-6-ethoxycarbonyl aminobenzotriazole as an intermediate A stirred solution of 3.5 grams (0.014 mole) of 2-(2-propen-1-ylamino)-4-ethoxycarbonylamino-5-fluoroaniline in 100 mL of aqueous 1% sulfuric acid was cooled to about −5° C., and a solution of 1.9 grams (0.028 mole) of sodium nitrite dissolved in a minimum of water was added dropwise, while the reaction mixture temperature was held at about 0°–10° C. Upon completion of the addition, the reaction mixture was stirred for one hour and then poured into water. The mixture was made basic to a pH of 8 with potassium carbonate. The mixture was then extracted thoroughly with ethyl acetate. The combined extracts were washed with an aqueous solution saturated with sodium chloride, and then dried with magnesium sulfate. The mixture was filtered, and the filtrate was subjected to column chromatography on silica gel. Elution was accomplished with 1:3 ethyl acetate in hexane. The product-containing fractions were combined and concentrated under reduced pressure, yielding 0.8 gram of 1-(2-propen-1-yl)-5-fluoro-6-ethoxycarbonylaminobenzotriazole. The NMR spectrum was consistent with the proposed structure.

Step D Synthesis of 3-[1-(2-propen-1-yl)-5-fluorobenzotriazol-6-yl]-6-trifluoromethyluracil as an intermediate This compound was prepared in a manner analogous to that of Step G of Example 1, using 0.8 gram (0.003 mole) of 1-(2-propen-1-yl)-5-fluoro-6-ethoxycarbonylaminobenzotriazole, 0.6 gram (0.003 mole) of ethyl 3-amino-4,4,4-trifluoro-2-butenoate, 0.2 gram (0.004 mole) of sodium methoxide, and 0.15 mL (catalyst) of 1,8-diazabicyclo[5.4.0]undec-7-ene (DBU) in 30 mL of N,N-dimethylformamide. The yield of 3-[1-(2-propen-1-yl)-2-trifluoromethyl-5-fluorobenzotriazol-6-yl]-6-trifluoromethyluracil was 0.8 gram. The NMR spectrum was consistent with the proposed structure.

Step E Synthesis of 1-methyl-3-[1-(2-propen-1-yl)-5-fluorobenzotriazol-6-yl]-6-trifluoromethyluracil (Compound 24)

This compound was prepared in a manner analogous to that of Step H of Example 1, using 0.8 gram (0.002 mole) of 3-[1-(2-propen-1-yl)-5-fluorobenzotriazol-6-yl]-6-trifluoromethyluracil, 0.6 gram (0.005 mole) of potassium carbonate, and 0.49 mL (0.005 mole) of methyl iodide in 15 mL of acetone. The yield of 1-methyl-3-[1-(2-propen-1-yl)-5-fluorobenzotriazol-6-yl]-6-trifluoromethyluracil was 0.3 gram, mp 136°–138° C. The NMR spectrum was consistent with the proposed structure.

EXAMPLE 7

SYNTHESIS OF 3-[1-(2-METHYLPROPYL)-2-TRIFLUOROMETHYLBENZIMIDAZOL-6-YL]-6-TRIFLUOROMETHYLURACIL (COMPOUND 16)

Step A Synthesis of N-ethoxycarbonyl-3-chloro-4-nitroaniline as an intermediate

This compound was prepared in a manner analogous to that of Step D of Example 2, using 5.0 grams (0.029 mole) of 3-chloro-4-nitroaniline and 4.1 grams (0.038 mole) of ethyl chloroformate in 60 mL of pyridine. The yield of N-ethoxycarbonyl-3-chloro-4-nitroaniline was 5.9 grams, mp 124°–126° C. The NMR spectrum was consistent with the proposed structure.

Step B Synthesis of N-(2-methylpropyl)-5-ethoxycarbonylamino-2-nitroaniline as an intermediate This compound was prepared in a manner analogous to that of Step A of Example 1, using 5.4 grams (0.022 mole) of N-ethoxycarbonyl-3-chloro-4-nitroaniline, 2.4 grams (0.033 mole) of 2-methylpropylamine, and 20 mL of triethylamine in 100 mL of dioxane. The yield of N-(2-methylpropyl)-5-ethoxycarbonylamino-2-nitroaniline was 3.5 grams, mp 112°–115° C. The NMR spectrum was consistent with the proposed structure.

Step C Synthesis of 2-(2-methylpropylamino)-4-(ethoxycarbonylamino)aniline as an intermediate This compound was prepared in a manner analogous to that of Step F of Example 2, using 3.5 grams (0.013 mole) of N-(2-methylpropyl)-5-ethoxycarbonylamino-2-nitroaniline, 2.8 grams (0.050 mole) of iron powder, 15 mL of acetic acid, and 1.0 mL (0.014 mole) of concentrated hydrochloric acid in 100 mL of ethanol. The yield of 2-(2-methylpropylamino)-4-(ethoxycarbonylamino)aniline was 3.0 grams. The NMR spectrum was consistent with the proposed structure.

Step D Synthesis of a mixture of N-trifluoromethylcarbonyl-2-[(trifluoromethylcarbonyl)(2-methylpropyl)amino]-4-(ethoxycarbonylamino)aniline and 1-(2-methylpropyl)-2-trifluoromethyl-6-ethoxycarbonylaminobenzimidazole as intermediates This reaction was conducted in a manner analogous to that of Step G of Example 2, using 3.0 grams (0.012 mole) of 2-(2-methylpropylamino)-4-(ethoxycarbonylamino)aniline and 1.9 mL (0.020 mole) of trifluoroacetic anhydride in about 90 mL of toluene. The reaction product was subjected to column chromatography on silica gel, with 1:1 ethyl acetate in hexane as the eluant. The product-containing fractions were combined and concentrated under reduced pressure, yielding about 4.0 grams of product. NMR analysis of the product indicated that it was a 1:1 mixture of the intended 1-(2-methylpropyl)-2-trifluoromethyl-6-ethoxycarbonylaminobenzimidazole intermediate, and an uncyclized intermediate, N-trifluoromethylcarbonyl-2-[(trifluoromethylcarbonyl)(2-methylpropyl)amino]-4-(ethoxycarbonylamino)aniline.

Step E Synthesis of 1-(2-methylpropyl)-2-trifluoromethyl-6-ethoxycarbonylaminobenzimidazole as an intermediate This compound was prepared in a manner analogous to that of Step D of Example 3, by the treatment of the 1:1 mixture of N-trifluoromethylcarbonyl-2-[(trifluoromethylcarbonyl)(2-methylpropyl)amino]-4-(ethoxycarbonylamino)aniline and 1-(2-methylpropyl)-2-trifluoromethyl-6-ethoxycarbonylaminobenzimidazole, which contained about 2.0 grams (0.005 mole) of the substituted aniline, with 0.6 gram (0.005 mole) of potassium carbonate (dissolved in a small amount of water) in 60 mL of methanol. NMR analysis of the reaction mixture indicated that ring closure of the substituted aniline derivative had occurred, yielding a total of about 2.5 grams of the 1-(2-methylpropyl)-2-trifluoromethyl-6-ethoxycarbonylaminobenzimidazole intermediate. The NMR spectrum was consistent with the proposed structure.

Step F Synthesis of 3-[1-(2-methylpropyl)-2-trifluoromethylbenzimidazol-6-yl]-6-trifluoromethyluracil as an intermediate This compound was prepared in a manner analogous to that of Step G of Example 1, using 2.0 grams (0.006 mole) of 1-(2-methylpropyl)-2-trifluoromethyl-6-ethoxycarbonylaminobenzimidazole, 1.1 grams (0.006 mole) of ethyl 3-amino-4,4,4-trifluoro-2-butenoate, 0.4 gram (0.007 mole) of sodium methoxide, and 0.3 mL (catalyst) of 1,8-diazabicyclo[5.4.0]undec-7-ene (DBU) in 100 mL of N,N-dimethylformamide. The yield of 3-[1-(2-methylpropyl)-2-trifluoromethylbenzimidazol-6-yl]-6-trifluoromethyluracil was 1.0 gram, mp>200° C. The NMR spectrum was consistent with the proposed structure.

Step G Synthesis of 1-methyl-3-[1-(2-methylpropyl)-2-trifluoromethylbenzimidazol-6-yl]-6-trifluoromethyluracil (Compound 16)

This compound was prepared in a manner analogous to that of Step H of Example 1, using 0.8 gram (0.002 mole) of 3-[1-(2-methylpropyl)-2-trifluoromethylbenzimidazol-6-yl]-6-trifluoromethyluracil, 0.5 gram (0.004 mole) of potassium carbonate, and 0.53 gram (0.005 mole) of methyl iodide in 50 mL of acetone. The yield of 1-methyl-3-[1-(2-methylpropyl)-2-trifluoromethylbenzimidazol-6-yl]-6-trifluoromethyluracil was 0.5 gram, mp 156°–159° C. The NMR spectrum was consistent with the proposed structure.

EXAMPLE 8

SYNTHESIS OF 1-METHYLETHYL 2-[2-TRIFLUOROMETHYL-5-FLUORO-6-(1-METHYL-6-TRIFLUOROMETHYLURACIL-3-YL)BENZIMIDAZOL-1-YL]-PROPANOATE (COMPOUND 20)

Step A Synthesis of 2-[2-trifluoromethyl-5-fluoro-6-(1-methyl-6-trifluoromethyluracil-3-yl)benzimidazol-1-yl]propan-1-ol (Compound 7) as an intermediate One hundred mL of methylene chloride was stirred and cooled to about –40° C. To this was added dropwise 11.0 mL (0.011 mole) of boron tribromide (1.0M in methylene chloride). Upon completion of the addition, the reaction mixture was again cooled to –40° C., and a solution of 4.5 grams (0.010 mole) of 1-methyl-3-(1-methoxymethylethyl-2-trifluoromethyl-5-fluorobenzimidazol-6-yl)-6-trifluoromethyluracil (Compound 8—prepared in a manner analogous to that of Example 3) in about 20 mL of methylene chloride was added dropwise. Upon completion of the addition, the reaction mixture was stirred for an additional one hour at –40° C. After this time the reaction mixture was allowed to warm to ambient temperature, where it stirred for about 18 hours. The reaction mixture was then poured into a flask, and ice was added. The mixture was stirred until the ice melted, and then extracted with ethyl acetate. The combined extracts were washed with an aqueous solution saturated with sodium chloride and dried with magnesium sulfate. The mixture was filtered, and the filtrate was concentrated under reduced pressure, yielding 4.3 grams of 2-[2-trifluoromethyl-5-fluoro-6-(1-methyl-6-trifluoromethyluracil-3-yl)benzimidazol-1-yl]propan-1-ol. The NMR spectrum was consistent with the proposed structure.

Step B Synthesis of 2-[2-trifluoromethyl-5-fluoro-6-(1-methyl-6-trifluoromethyluracil-3-yl)benzimidazol-1-yl] propanoic acid (Compound 19) as an intermediate Under a nitrogen atmosphere, 4.3 grams (0.010 mole) of 2-[2-trifluoromethyl-5-fluoro-6-(1-methyl-6-trifluoromethyluracil-3-yl) benzimidazol-1-yl]propan-1-ol in 120 mL of acetone was stirred, and 16 mL chromic acid (prepared by dissolving about five grams of chromium trioxide in 12 mL of water, then adding five mL of concentrated sulfuric acid), was added dropwise during a one hour period. Upon completion of the addition, the reaction mixture was stirred at ambient temperature for about 18 hours. The reaction was quenched with about three mL of 1-methylethanol, and the mixture was made basic with an aqueous solution saturated with sodium bicarbonate. The mixture was filtered to remove chromium salts, and the filtrate was extracted with ethyl acetate. The combined extracts were then washed with an aqueous solution saturated with sodium chloride. The organic layer was dried with sodium sulfate and filtered. The filtrate was concentrated under reduced pressure, yielding 3.0 grams of 2-[2-trifluoromethyl-5-fluoro-6-(1-methyl-6-trifluoromethyluracil-3-yl)benzimidazol-1-yl]propanoic acid. The NMR spectrum was consistent with the proposed structure.

Step C Synthesis of 1-methylethyl 2-[2-trifluoromethyl-5-fluoro-6-(1-methyl-6-trifluoromethyluracil-3-yl) benzimidazol-1-yl]propanoate (Compound 20)

A stirred mixture of 0.7 gram (0.002 mole) of 2-[2-trifluoromethyl-5-fluoro-6-(1-methyl-6-trifluoromethyluracil-3-yl)benzimidazol-1-yl]propanoic acid, 0.1 mL of concentrated sulfuric acid, and 1.0 gram of molecular sieves (synthetic zeolites, 4 to 8 mesh, pore size 4 angstroms) in 1-methylethanol was heated at reflux for about 18 hours. After this time, the reaction mixture was cooled and concentrated under reduced pressure to a residue. The residue was dissolved in ethyl acetate and washed with an aqueous solution saturated with sodium bicarbonate and then with an aqueous solution saturated with sodium chloride. The organic layer was dried with magnesium sulfate and filtered. The filtrate was concentrated under reduced pressure to a residual oil, which was triturated with petroleum ether, yielding solid 1-methylethyl 2-[2-trifluoromethyl-5-fluoro-6-(1-methyl-6-trifluoromethyluracil-3-yl)benzimidazol-1-yl]propanoate, mp 133°–135° C. The NMR spectrum was consistent with the proposed structure.

EXAMPLE 9

SYNTHESIS OF 1-METHYL-3-[1-(1-METHYL-2-CHLOROETHYL)-2-TRIFLUOROMETHYL-5-FLUOROBENZIMIDAZOL-6-YL]-6-TRIFLUOROMETHYLURACIL (COMPOUND 17)

Under a nitrogen atmosphere, a stirred solution of 0.4 gram (0.0009 mole) of 2-[2-trifluoromethyl-5-fluoro-6-(1-methyl-6-trifluoromethyluracil-3-yl)benzimidazol-1-yl] propan-1-ol (Compound 7—prepared as in Step A of Example 8) in 10 mL of diethyl ether was cooled in an ice-water bath, and 0.07 mL (0.0009 mole) of pyridine was added at a rate to maintain the reaction mixture temperature below 5° C. Upon completion of the addition, 0.1 mL (0.0013 mole) of thionyl chloride was added dropwise from a syringe. Upon completion of the addition, the reaction mixture stirred at about 0° C. for 30 minutes. After this time, the reaction mixture was allowed to warm to ambient temperature, where it stirred for about 18 hours. Analysis of the reaction mixture by thin layer chromatography (TLC) indicated the reaction was not complete. The reaction mixture was concentrated under reduced pressure to a residue. The residue was dissolved in methylene chloride, and 0.1 mL of thionyl chloride and 0.07 mL of pyridine were added. The mixture was warmed to reflux, where it stirred for about 24 hours. Analysis of the reaction mixture using TLC indicated the reaction was still not complete. Additional equivalents of thionyl chloride and pyridine were were added to the reaction mixture each day for a period of five days, as the reaction mixture stirred at reflux. At the end of five days the reaction mixture was allowed to cool to ambient temperature, where it stirred for two days. The reaction mixture was then poured into water and extracted with ethyl acetate. The extract was washed with an aqueous solution saturated with sodium chloride and dried with sodium sulfate. The mixture was filtered, and the filtrate concentrated under reduced pressure, yielding about 0.3 gram of 1-methyl-3-[1-(1-methyl-2-chloroethyl)-2-trifluoromethyl-5-fluorobenzimidazol-6-yl]-6-trifluoromethyluracil, mp 93°–95° C. The NMR spectrum was consistent with the proposed structure.

EXAMPLE 10

SYNTHESIS OF N-PHENYLMETHYL-2-[2-TRIFLUOROMETHYL-5-FLUORO-6-(1-METHYL-6-TRIFLUOROMETHYLURACIL-3-YL) BENZIMIDAZOL-1-YL] PROPANECARBOXAMIDE (COMPOUND 22)

Under a nitrogen atmosphere, a solution of 0.7 gram (0.0015 mole) of 2-[2-trifluoromethyl-5-fluoro-6-(1-methyl-6-trifluoromethyluracil-3-yl)benzimidazol-1-yl] propanoic acid (Compound 19—prepared as in Step B of Example 8) in 20 mL of methylene chloride was stirred, and 0.4 gram (0.0030 mole) of 1-hydroxybenzotriazole, then 0.5 gram (0.0030 mole) of 1-(3-dimethylaminopropyl)-3-ethylcarbodiimide hydrochloride were added. The reaction mixture was cooled to about 0° C., and 0.2 gram (0.0015 mole) of N-(phenylmethyl)amine was added. Upon completion of the addition, the reaction mixture was allowed to warm to ambient temperature, where it stirred for about 72 hours. The reaction mixture was then poured into water and extracted with methylene chloride. The combined extracts were washed with an aqueous solution saturated with sodium chloride. The organic layer was dried with magnesium sulfate and filtered. The filtrate was concentrated under reduced pressure to a residual oil, which was subjected to column chromatography on silica gel, with 1:2 ethyl acetate/hexane as the eluant. The product-containing fractions were combined and concentrated under reduced pressure, yielding 0.5 gram of N-phenylmethyl-2-[2-trifluoromethyl-5-fluoro-6-(1-methyl-6-trifluoromethyluracil-3-yl)benzimidazol-1-yl]propanecarboxamide; mp 191°–193° C. The NMR spectrum was consistent with the proposed structure.

Example 11

SYNTHESIS OF 1-AMINO-3-[1-(2-METHYLPROPYL)-2-TRIFLUOROMETHYL-5-FLUOROBENZIMIDAZOL-6-YL]-6-TRIFLUOROMETHYLURACIL (Compound 33)

Step A Synthesis of 1,1-dimethylethyl N-(2,4,6-trimethylphenylsulfonyloxy)carbamate as an intermediate A stirred solution of 25.0 grams (0.114 mole) of 2,4,6-trimethylbenzenesulfonyl chloride and 15.3 grams (0.114 mole) of 1,1-dimethylethyl N-hydroxycarbamate in 350 mL of diethyl ether was cooled in an ice-water bath, and 11.4 grams (0.114 mole) of triethylamine was added dropwise. Upon completion of the addition, the reaction mixture was allowed to warm to ambient temperature as it stirred for about 18 hours. The reaction mixture was then filtered, and the filtrate was concentrated under reduced pressure to a residue, which was slurried with toluene and petroleum ether. The resultant solid was collected by filtration, yielding 25.0 grams of 1,1-dimethylethyl N-(2,4,6-trimethylphenylsulfonyloxy)carbamate. The NMR spectrum was consistent with the proposed structure.

Step B Synthesis of 1-aminooxysulfonyl-2,4,6-trimethylbenzene as an intermediate Trifluoroacetic acid, 80.0 mL, was stirred and cooled in an ice-water bath, and 25.0 grams (0.079 mole) of 1,1-dimethylethyl N-(2,4,6-trimethylphenylsulfonyloxy) carbamate was added portionwise. Upon completion of the addition, the reaction mixture was stirred for 90 minutes, then poured into ice-water The resultant solid was collected by filtration and dissolved in diethyl ether. The solution was dried with magnesium sulfate and filtered. The solid product was precipitated from the filtrate by the addition of petroleum ether. The solid was collected by filtration, yielding 14.4 grams of 1-aminooxysulfonyl-2,4,6-trimethylbenzene. The NMR spectrum was consistent with the proposed structure.

Step C Synthesis of 1-amino-3-[1-(2-methylpropyl)-2-trifluoromethyl-5-fluorobenzimidazol-6-yl]-6-trifluoromethyluracil (Compound 33)

A solution of 1.3 grams (0.003 mole) of 3-[1-(2-methylpropyl)-2-trifluoromethyl-5-fluorobenzimidazol-6-yl]-6-trifluoromethyluracil (prepared as in Example 2, Steps A–H) in 30 mL of tetrahydrofuran is stirred, and 0.5 gram (0.003 mole) of potassium carbonate, then 0.7 gram (0.003 mole) of 1-aminooxysulfonyl-2,4,6-trimethylbenzene are added. Upon completion of the addition, the reaction mixture is stirred for one hour. The reaction mixture is then diluted with water and extracted with three portions of ethyl acetate. The combined extracts are dried with magnesium sulfate and filtered. The filtrate is concentrated under reduced pressure to a residue, which is purified by column chromatography, yielding 1-amino-3-[1-(2-methylpropyl)-2-trifluoromethyl-5-fluorobenzimidazol-6-yl]-6-trifluoromethyluracil.

The compounds described in Table 1 were prepared by methods similar to those set forth above. Characterizing data for these compounds are given in Table 2.

HERBICIDAL ACTIVITY

The herbicides of this invention were tested for pre- and postemergence herbicidal activity using a variety of crops and weeds. The test plants included soybean (*Glycine max* var. Williams), field corn (*Zea mays* var. Agway 425X), wheat (*Triticum aestivum* var. Wheaton), morningglory (*Ipomoea lacunosa* or *Ipomoea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium pensylvanicum*). For preemergence testing, two disposable fiber flats (8 cm×15 cm×25 cm) for each rate of application of each candidate herbicide were filled to an approximate depth of 6.5 cm With steam-sterilized sandy loam soil. The soil was leveled and impressed with a template to provide five evenly spaced furrows 13 cm long and 0.5 cm deep in each flat. Seeds of soybean, wheat, corn, green foxtail, and Johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 8–12 days prior to the preemergence flats and were placed in a greenhouse and watered, thus allowing the seeds to germinate and the foliage to develop.

In both pre- and postemergence tests, a stock solution of the candidate herbicide was prepared by dissolving a predetermined weight of the compound in 20 mL of water/acetone (50/50) containing 0.5% v/v sorbitan monolaurate. Thus for an application rate of up to 3000 g/ha of herbicide, 0.27 g of candidate herbicide was dissolved in 20 mL of the aqueous acetone to prepare the stock solution. A portion (10 mL) was then diluted with water/acetone (50/50) to 45 mL, the volume required to correspond to a spray volume of 1000 L/ha. The remaining stock solution was then used to prepare solutions for lower application rates.

For the 0.3 kg/ha rate reported in Tables 3 and 4, 1.0 mL of stock solution was diluted with 44 mL of water/acetone (50/50) to 45 mL.

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 17–21 days the plants were examined and the phytotoxicity data were recorded.

Herbicidal activity data are given in Table 3 and Table 4 for various 3-(bicyclic nitrogen-containing heterocycle)-substituted-1-methyl-6-trifluoromethyluracils. From these data it is clear that a variety of R substituents give compounds having fair to excellent herbicidal activity, whereas when V is $R^1$, any deviation from the preferred —$CF_3$ group for $R^1$ results in a marked decrease in herbicidal avtivity. The test compounds are identified by numbers that correspond to those in Table 1, where the numbers for particularly preferred compounds of the invention are underlined.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Alabama, 1977. The rating system is as follows:

Herbicide Rating System

| Rating Percent Control | Description of Main Categories | Crop/Weed Description | Description |
|---|---|---|---|
| 0 | No effect | No crop No weed reduction or injury | control |
| 10 | Slight effect | Slight discoloration- or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application the active compounds of the invention are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. A wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently additional wetting agent(s) and/or oil will be added to the tank mix for postemergence application to facilitate dispersion on the foliage and absorption by the plant.

Other useful formulations for herbicidal applications are emulsifiable concentrates (ECs), which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and the sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent(s), when used, normally comprises from 1 to 15% by weight of the composition.

Other useful formulations include suspensions of the active ingredient in a relatively non-volatile liquid such as water, corn oil, kerosene, propylene glycol, or other suitable liquid carrier.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granule are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful with the present herbicidal compounds. For use by the farmer on the field, the granular formulations, emulsifiable concentrates, flowable concentrates, solutions, etc., may be diluted with water to give a concentration of active ingredient in the range of, say, 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is, of course, employed; the amount may be as low as, e.g., about 10 to 100 g/ha, preferably about 30 to 60 g/ha. For field use, where there are losses of herbicide, higher application rates (e.g., four times the greenhouse testing rates mentioned above) may be employed.

The active herbicidal compounds of this invention may be used in combination with other herbicides, e.g., they may be mixed with, say, a lesser, equal, or larger amount of a known herbicide such as aryloxyalkanoic acid herbicides such as (2,4-dichlorophenoxy)acetic acid (2,4-D), (4-chloro-2-methylphenoxy)acetic acid (MCPA), (±)-2-(4-chloro-2-methylphenoxy)-propanoic acid (MCPP); urea herbicides, such as N,N-dimethyl-N'-[4-(1-methylethyl)phenyl]urea (isoproturon); imidazolinone herbicides, such as 2-[4,5-dihydro-4-methyl-4-(1-methylethyl)-5-oxo-1 H-imidazol-2-yl]-3-pyridinecarboxylic acid (imazapyr), a reaction product comprising (±)-2-[4,5-dihydro-4-methyl-4-(1-methylethyl)-5-oxo-1 H-imidazol-2-yl]-4-methylbenzoic acid and (±)-2-[4,5-dihydro-4-methyl-4-(1-methylethyl)-5-oxo-1 H-imidazol-2-yl]-5-methylbenzoic acid (imazamethabenz), (±)-2-[4,5-dihydro-4-methyl-4-(1-methylethyl)-5-oxo-1 H-imidazol-2-yl]-5-ethyl-3-pyridinecarboxylic acid (imazethapyr), and (±)-2-[4,5-dihydro-4-methyl-4-(1-methylethyl)-5-oxo-1 H-imidazol-2-yl]-3-quinolinecarboxylic acid (imazaquin); diphenyl ether herbicides, such as 5-[2-chloro-4-(trifluoromethyl) phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2-pyrimidinyl)amino]carbonyl]amino] sulfonyl]benzoic acid (chlorimuron), 2-chloro-N-[[(4-methoxy-6-methyl-1,3,5-triazin-2-yl)amino]carbonyl] benzenesulfonamide (chlorsulfuron), 2-[[[[(4,6-dimethoxy-2-pyrimidinyl)amino]carbonyl]amino]sulfonyl]methyl] benzoic acid (bensulfuron), 2-[[[[(4,6-dimethoxy-2-pyrimidinyl)amino]carbonyl]amino]sulfonyl]-1-methyl-1 H-pyrazol-4-carboxylic acid (pyrazosulfuron), 3-[[[[(4-methoxy-6-methyl-1,3,5-triazin-2-yl)amino]carbonyl] amino]sulfonyl]-2-thiophenecarboxylic acid (thifensulfuron), and 2-(2-chloroethoxy)-N-[[(4-methoxy-6-methyl-1,3,5-triazin-2-yl)amino]carbonyl] benzenesulfonamide (triasulfuron); 2-(4-aryloxyphenoxy) alkanoic acid herbicides, such as (±)-2-[4-[(6-chloro-2-benzoxazolyl)oxy]phenoxy]propanoic acid (fenoxaprop), (±)-2-[4-[[5-(trifluoromethyl)-2-pyridinyl]oxy]phenoxy] propanoic acid (fluazifop), (±)-2-[4-(6-chloro-2-quinoxalinyl)oxy]phenoxy]propanoic acid (quizalofop), and (±)-2-[-(2,4-dichlorophenoxy)phenoxy]propanoic acid (diclofop); benzothiadiazinone herbicides, such as 3-(1-methylethyl)-1 H-2,1,3-benzothiadiazin-4(3 H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

3-(Bicyclic Nitrogen-containing Heterocycle)-substituted 1-Substituted-6-trifluoromethyluracils as Herbicides

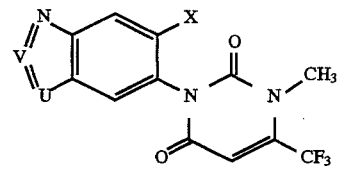

| Cmpd. No. | R | $R^1$ | X |
|---|---|---|---|
| V = $CR^1$ | | | |
| 1* | H | $-CF_3$ | H |
| 2 | n-$C_3H_7$ | H | F |
| 3 | n-$C_3H_7$ | $-CH_3$ | F |
| 4 | n-$C_3H_7$ | $-CF_3$ | F |
| 5 | n-$C_3H_7$ | $-CF_2CF_3$ | F |
| 6 | $-CH_2CH(CH_3)_2$ | $-CF_3$ | F |
| 7 | $-CH(CH_3)CH_2OH$ | $-CF_3$ | F |
| 8 | $-CH(CH_3)CH_2OCH_3$ | $-CF_3$ | F |
| 9 | $-CH_2CH=CH_2$ | $-CF_3$ | H |
| 10 | $-CH_2CH=CH_2$ | $-CF_3$ | F |
| 11 | $-CH_2C\equiv CH$ | $-CF_3$ | F |
| 12 | benzyl | $-CF_3$ | F |
| 13 | 2-chlorobenzyl | $-CF_3$ | F |
| 14 | 3-chlorobenzyl | $-CF_3$ | F |
| 15 | 4-chlorobenzyl | $-CF_3$ | F |
| 16 | $-CH_2CH(CH_3)_2$ | $-CF_3$ | H |
| 17 | $-CH(CH_3)CH_2Cl$ | $-CF_3$ | F |
| 18 | $-CH(CH_3)CH_2OCH_3$ | $-CF_3$ | H |
| 19 | $-CH(CH_3)CO_2H$ | $-CF_3$ | F |
| 20 | $-CH(CH_3)CO_2CH(CH_3)_2$ | $-CF_3$ | F |
| 21 | $-CH(CH_3)C(=O)N(CH_3)_2$ | $-CF_3$ | F |

TABLE 1-continued 3-(Bicyclic Nitrogen-containing Heterocycle)-substituted 1-Substituted-6-trifluoromethyluracils as Herbicides

| 22 | (isopropyl-C(O)-NH-CH2-phenyl) | —CF₃ | F |

V = N

| 23 | n-C₃H₇ | | F |
| 24 | —CH₂CH=CH₂ | | F |
| 25 | —CH₂-phenyl | | F |
| 26 | —CH(CH₃)CH₂OCH₃ | | F |
| 27 | —CH₂CH=CH₂ | | H |

Structure with benzotriazole fused ring system, R, R¹, X, R² substituents, CF₃ group

| Cmpd. No. | R | R¹ | X | R² |
|---|---|---|---|---|

V = CR¹

| 28 | —CH(CH₃)C₂H₅ | —CF₃ | F | —CH₃ |
| 29 | —CH(CH₃)CH₂CH(CH₃)₂ | —CF₃ | F | —CH₃ |
| 30 | —CH(CH₃)CH₂O-phenyl | —CF₃ | F | —CH₃ |
| 31 | —CH(CH₃)CO₂C₂H₅ | —CF₃ | F | —CH₃ |
| 32 | —CH₂CH(CH₃)OCH₃ | —CF₃ | F | —CH₃ |
| 33 | —CH₂CH(CH₃)₂ | —CF₃ | F | —NH₂ |
| 34 | —CH₂CH(CH₃)₂ | —CN | F | —CH₃ |

*Compound 1 is a tautomeric mixture

TABLE 2

EMPIRICAL FORMULA/CHARACTERIZING DATA

| Cmpd No | Empirical Formula | Melting Point (°C.)/ Physical State |
|---|---|---|
| 1 | 2C₁₄H₈F₆N₄O₂ | >200 |
| 2 | C₁₆H₁₄F₄N₄O₂ | 78–80 |
| 3 | C₁₇H₁₆F₄N₄O₂ | OIL |
| 4 | C₁₇H₁₃F₇N₄O₂ | 162 |
| 5 | C₁₈H₁₃F₉N₄O₂ | 65–67 |
| 6 | C₁₈H₁₅F₇N₄O₂ | 169–170 |
| 7 | C₁₇H₁₃F₇N₄O₃ | 109–111 |
| 8 | C₁₈H₁₅F₇N₄O₃ | 173–174 |
| 9 | C₁₇H₁₂F₈N₄O₂ | 171–173 |
| 10 | C₁₇H₁₁F₇N₄O₂ | 131–132 |
| 11 | C₁₇H₉F₇N₄O₂ | 104–105 |
| 12 | C₂₁H₁₃F₇N₄O₂ | 115–117 |
| 13 | C₂₁H₁₂ClF₇N₄O₂ | 173–175 |
| 14 | C₂₁H₁₂ClF₇N₄O₂ | 91–93 |
| 15 | C₂₁H₁₂ClF₇N₄O₂ | 142–144 |
| 16 | C₁₈H₁₆F₆N₄O₂ | 156–159 |
| 17 | C₁₇H₁₂ClF₇N₄O₂ | 93–95 |
| 18 | C₁₈H₁₆F₆N₄O₃ | 78–80 |

TABLE 2-continued

EMPIRICAL FORMULA/CHARACTERIZING DATA

| Cmpd No | Empirical Formula | Melting Point (°C.)/ Physical State |
|---|---|---|
| 19 | C₁₇H₁₁F₇N₄O₄ | 135–137 |
| 20 | C₂₀H₁₇F₇N₄O₄ | 133–135 |
| 21 | C₁₉H₁₆F₇N₅O₃ | 110–112 |
| 22 | C₂₄H₁₈F₇N₅O₃ | 191–193 |
| 23 | C₁₅H₁₃F₄N₅O₂ | 172–174 |
| 24 | C₁₅H₁₁F₄N₅O₂ | 136–138 |
| 25 | C₁₉H₁₃F₄N₅O₂ | 184–186 |
| 26 | C₁₆H₁₅F₄N₅O₃ | 158–160 |
| 27 | C₁₅H₁₂F₃N₅O₂ | 183–186 |
| 28 | C₁₈H₁₅F₇N₄O₂ | 164–165 |
| 29 | C₂₀H₁₉F₇N₄O₂ | 70–72 |
| 30 | C₂₃H₁₇F₇N₄O₃ | 174–175 |
| 31 | C₁₉H₁₅F₇N₄O₄ | 89–91 |
| 32 | C₁₈H₁₅F₇N₄O₃ | |
| 33 | C₁₇H₁₄F₇N₅O₂ | |
| 34 | C₁₈H₁₅F₄N₅O₂ | |

TABLE 3

PREEMERGENCE HERBICIDAL ACTIVITY (% CONTROL)

| Cmpd. No. | 1 | 2 | 3 | 4 |
|---|---|---|---|---|
| Rate(kg/ha) | 0.3 | 0.3 | 0.3 | 0.3 |
| Species | | | | |
| Soybean | 10 | 30 | 0 | 100 |
| Wheat | 0 | 0 | 0 | 100 |
| Corn | 40 | 20 | 0 | 100 |
| Velvetleaf | 60 | 100 | 0 | 100 |
| Morningglory | 100 | 95 | 0 | 100 |
| Chickweed | 100 | 95 | 0 | — |
| Cocklebur | 10 | 40 | 0 | 100 |
| Blackgrass | 30 | 20 | 0 | 100 |
| Green foxtail | 60 | 95 | 0 | 100 |
| Johnsongrass | 70 | 90 | 30 | 100 |

| Cmpd. No. | 5 | 6 | 7 | 8 |
|---|---|---|---|---|
| Rate(kg/ha) | 0.3 | 0.3 | 0.3 | 0.3 |
| Species | | | | |
| Soybean | 10 | 100 | 100 | 100 |
| Wheat | 0 | 100 | 80 | 100 |
| Corn | 60 | 100 | 100 | 100 |
| Velvetleaf | 100 | 100 | 100 | 100 |
| Morningglory | 0 | 100 | 100 | 100 |
| Chickweed | 100 | 100 | 100 | 100 |
| Cocklebur | 0 | 80 | 100 | 100 |
| Blackgrass | 0 | 100 | 80 | 100 |
| Green foxtail | 60 | 100 | 100 | 100 |
| Johnsongrass | 70 | 100 | 100 | 100 |

| Cmpd. No. | 9 | 10 | 11 | 12 |
|---|---|---|---|---|
| Rate(kg/ha) | 0.3 | 0.3 | 0.3 | 0.3 |
| Species | | | | |
| Soybean | 100 | 100 | 100 | 10 |
| Wheat | 70 | 100 | 50 | 40 |
| Corn | 95 | 100 | 100 | 90 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 20 |
| Blackgrass | 100 | 100 | 20 | 70 |
| Green foxtail | 100 | 100 | 100 | 100 |
| Johnsongrass | 100 | 100 | 100 | 100 |

TABLE 3-continued

PREEMERGENCE HERBICIDAL ACTIVITY (% CONTROL)

| Cmpd. No. | 13 | 14 | 15 | 16 |
|---|---|---|---|---|
| Rate(kg/ha) | 0.3 | 0.3 | 0.3 | 0.3 |
| Species | | | | |
| Soybean | 50 | 20 | 0 | 100 |
| Wheat | 50 | 20 | 10 | 100 |
| Corn | 80 | 70 | 40 | 100 |
| Velvetleaf | 100 | 100 | 60 | 100 |
| Morningglory | 100 | 50 | 30 | 100 |
| Chickweed | 100 | 100 | | — |
| Cocklebur | 30 | 10 | 70 | 50 |
| Blackgrass | 70 | 30 | 10 | 70 |
| Green foxtail | 100 | 100 | 70 | 100 |
| Johnsongrass | 100 | 80 | 80 | 100 |

| Cmpd. No. | 18 | 19 | 20 | 21 |
|---|---|---|---|---|
| Rate(kg/ha) | 0.3 | 0.3 | 0.3 | 0.3 |
| Species | | | | |
| Soybean | 100 | 0 | 100 | 100 |
| Wheat | 90 | 0 | 60 | 50 |
| Corn | 100 | 20 | 95 | 95 |
| Velvetleaf | 100 | 70 | 100 | 100 |
| Morningglory | 100 | 100 | 100 | 100 |
| Chickweed | 100 | 70 | 100 | 100 |
| Cocklebur | 100 | 0 | 70 | 100 |
| Blackgrass | 100 | 0 | 70 | 70 |
| Green foxtail | 100 | 60 | 100 | 100 |
| Johnsongrass | 100 | 50 | 100 | 100 |

| Cmpd. No. | 22 | 23 | 24 | 25 |
|---|---|---|---|---|
| Rate(kg/ha) | 0.3 | 0.3 | 0.3 | 0.3 |
| Species | | | | |
| Soybean | 100 | 100 | 100 | 100 |
| Wheat | 70 | 100 | 100 | 80 |
| Corn | 100 | 100 | 100 | 95 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 95 | 100 | 95 |
| Blackgrass | 60 | 100 | 100 | 100 |
| Green foxtail | 100 | 100 | 100 | 100 |
| Johnsongrass | 100 | 100 | 100 | 100 |

| Cmpd. No. | 26 | 27 | 28 | 29 |
|---|---|---|---|---|
| Rate(kg/ha) | 0.3 | 0.3 | 0.3 | 0.3 |
| Species | | | | |
| Soybean | 100 | 100 | 100 | 70 |
| Wheat | 100 | 80 | 95 | 30 |
| Corn | 100 | 100 | 100 | 80 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 95 | 80 | 25 |
| Blackgrass | 100 | 70 | 100 | 60 |
| Green foxtail | 100 | 100 | 100 | 100 |
| Johnsongrass | 100 | 100 | 100 | 90 |

| Cmpd. No. | 30 | 31 |
|---|---|---|
| Rate(kg/ha) | 0.3 | 0.3 |
| Species | | |
| Soybean | 10 | 100 |
| Wheat | 10 | 100 |
| Corn | 60 | 100 |
| Velvetleaf | 95 | 100 |
| Morningglory | 80 | 100 |
| Chickweed | 100 | 100 |
| Cocklebur | 20 | 100 |
| Blackgrass | 10 | 95 |
| Green foxtail | 80 | 100 |
| Johnsongrass | 60 | 100 |

TABLE 4

POSTEMERGENCE HERBICIDAL ACTIVITY (% CONTROL)

| Cmpd. No. | 1 | 2 | 3 | 4 |
|---|---|---|---|---|
| Rate(kg/ha) | 0.3 | 0.3 | 0.3 | 0.3 |
| Species | | | | |
| Soybean | 60 | 90 | 20 | 95 |
| Wheat | 0 | 10 | 0 | 80 |
| Corn | 60 | 30 | 20 | 100 |
| Velvetleaf | 20 | 80 | 80 | 100 |
| Morningglory | 80 | 70 | 0 | 100 |
| Chickweed | 100 | 10 | 100 | 100 |
| Cocklebur | 20 | 50 | 10 | 95 |
| Blackgrass | 10 | 10 | — | 70 |
| Green foxtail | 60 | 95 | 0 | 100 |
| Johnsongrass | 60 | 30 | 0 | 100 |

| Cmpd. No. | 5 | 6 | 7 | 8 |
|---|---|---|---|---|
| Rate(kg/ha) | 0.3 | 0.3 | 0.3 | 0.3 |
| Species | | | | |
| Soybean | 20 | 95 | 100 | 100 |
| Wheat | 0 | 70 | 60 | 90 |
| Corn | 40 | 100 | 100 | 100 |
| Velvetleaf | 50 | 100 | 100 | 100 |
| Morningglory | 0 | 100 | 100 | 100 |
| Chickweed | 0 | 100 | 100 | 100 |
| Cocklebur | 20 | 100 | 100 | 100 |
| Blackgrass | 0 | 100 | 70 | 100 |
| Green foxtail | 30 | 100 | 100 | 100 |
| Johnsongrass | 40 | 100 | 90 | 100 |

| Cmpd. No. | 9 | 10 | 11 | 12 |
|---|---|---|---|---|
| Rate(kg/ha) | 0.3 | 0.3 | 0.3 | 0.3 |
| Species | | | | |
| Soybean | 95 | 95 | 95 | 80 |
| Wheat | 60 | 60 | 20 | 40 |
| Corn | 80 | 95 | 60 | 100 |
| Velvetleaf | 100 | 100 | 100 | 100 |
| Morningglory | 100 | 100 | 100 | 95 |
| Chickweed | 100 | 100 | 100 | 90 |
| Cocklebur | 95 | 100 | 100 | 90 |
| Blackgrass | 70 | 100 | 50 | 50 |
| Green foxtail | 100 | 100 | 100 | 100 |
| Johnsongrass | 100 | 100 | 90 | 100 |

| Cmpd. No. | 13 | 14 | 15 | 16 |
|---|---|---|---|---|
| Rate(kg/ha) | 0.3 | 0.3 | 0.3 | 0.3 |
| Species | | | | |
| Soybean | 70 | 70 | 40 | 95 |
| Wheat | 30 | 20 | 0 | 60 |
| Corn | 70 | 60 | 60 | 80 |
| Velvetleaf | 100 | 100 | 100 | 100 |
| Morningglory | 100 | 60 | 30 | 90 |
| Chickweed | 100 | 80 | 0 | 100 |
| Cocklebur | 100 | 70 | 60 | 100 |
| Blackgrass | 0 | 10 | 0 | 60 |
| Green foxtail | 100 | 90 | 90 | 100 |
| Johnsongrass | 80 | 90 | 60 | 95 |

| Cmpd. No. | 18 | 19 | 20 | 21 |
|---|---|---|---|---|
| Rate(kg/ha) | 0.3 | 0.3 | 0.3 | 0.3 |

(Table 3-continued, top of right column:)

| | | |
|---|---|---|
| Green foxtail | 80 | 100 |
| Johnsongrass | 60 | 100 |

TABLE 4-continued

| POSTEMERGENCE HERBICIDAL ACTIVITY (% CONTROL) | | | | |
|---|---|---|---|---|
| Species | | | | |
| Soybean | 100 | 50 | 100 | 95 |
| Wheat | 7 | 10 | 80 | 60 |
| Corn | 100 | 50 | 95 | 90 |
| Velvetleaf | 100 | 50 | 100 | 100 |
| Morningglory | 100 | 80 | 100 | 100 |
| Chickweed | 100 | 50 | 100 | — |
| Cocklebur | 100 | 20 | 95 | 100 |
| Blackgrass | 80 | 0 | 100 | 100 |
| Green foxtail | 90 | — | 100 | 100 |
| Johnsongrass | 100 | 50 | 100 | 100 |
| Cmpd. No. | 22 | 23 | 24 | 25 |
| Rate(kg/ha) | 0.3 | 0.3 | 0.3 | 0.3 |
| Species | | | | |
| Soybean | 100 | 100 | 95 | 95 |
| Wheat | 100 | 100 | 70 | 60 |
| Corn | 100 | 100 | 95 | 90 |
| Velvetleaf | 100 | 100 | 100 | 100 |
| Morningglory | 100 | 100 | 100 | 100 |
| Chickweed | 100 | 100 | 100 | — |
| Cocklebur | 95 | 100 | 100 | 100 |
| Blackgrass | 100 | 100 | 100 | 100 |
| Green foxtail | 100 | 100 | 100 | 100 |
| Johnsongrass | 100 | 100 | 100 | 100 |
| Cmpd. No. | 26 | 27 | 28 | 29 |
| Rate(kg/ha) | 0.3 | 0.3 | 0.3 | 0.3 |
| Species | | | | |
| Soybean | 100 | 100 | 95 | 70 |
| Wheat | 80 | 70 | 60 | 10 |
| Corn | 90 | 70 | 90 | 80 |
| Velvetleaf | 100 | 100 | 100 | 100 |
| Morningglory | 100 | 100 | 100 | 100 |
| Chickweed | — | — | 100 | 100 |
| Cocklebur | 100 | 80 | 100 | 100 |
| Blackgrass | 80 | 30 | 100 | 10 |
| Green foxtail | 100 | 80 | 100 | 100 |
| Johnsongrass | 100 | 90 | 100 | 90 |
| Cmpd. No. | 30 | 31 | | |
| Rate(kg/ha) | 0.3 | 0.3 | | |
| Species | | | | |
| Soybean | 30 | 95 | | |
| Wheat | 10 | 80 | | |
| Corn | 50 | 100 | | |
| Velvetleaf | 100 | 100 | | |
| Morningglory | 100 | 100 | | |
| Chickweed | 90 | 100 | | |
| Cocklebur | 30 | 100 | | |
| Blackgrass | 20 | 100 | | |
| Green foxtail | 60 | 100 | | |
| Johnsongrass | 40 | 100 | | |

I claim:
1. A compound of the formula

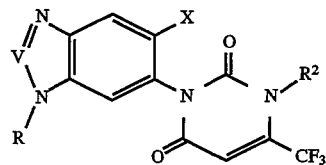

in which
V is N or C—$R^1$;
R is hydrogen, straight or branched chain alkyl, alkenyl, alkynyl, hydroxyalkyl, alkoxyalkyl, haloalkyl, alkoxycarbonylalkyl, phenylalkyl, optionally substituted with halogen, or aminocarbonylalkyl in which the amino nitrogen is substituted with phenylalkyl or one or two alkyl;
$R^1$ is hydrogen, alkyl, haloalkyl, or cyano;
$R^2$ is lower alkyl or amino; and
X is hydrogen or halogen,
with the proviso that each aliphatic component has not more than six carbon atoms.

2. A compound of claim 1 in which $R^2$ is methyl or amino, V is C—$CF_3$ or N, X is hydrogen or fluoro, and each aliphatic component has not more than four carbon atoms, and phenylalkyl is phenylmethyl.

3. A compound of claim 2 in which $R^2$ is methyl, V is C—$CF_3$ or N, and X is hydrogen.

4. The compound of claim 3 in which V is C—$CF_3$, and R is allyl.

5. The compound of claim 3 in which V is N, and R is allyl.

6. A compound of claim 2 in which $R^2$ is methyl, V is C—$CF_3$, and X is fluoro.

7. The compound of claim 6 in which R is 2-methylpropyl.

8. The compound of claim 6 in which R is allyl.

9. The compound of claim 6 in which R is propargyl.

10. The compound of claim 6 in which R is phenylmethyl.

11. The compound of claim 6 in which R is 2-methoxy-1-methylethyl.

12. The compound of claim 6 in which R is 2-chloro-1-methylethyl.

13. The compound of claim 6 in which R is 1-ethoxycarbonylethyl.

14. The compound of claim 6 in which R is 2-methoxypropyl.

15. A compound of claim 2 in which V is N, and X is fluoro.

16. The compound of claim 2 in which R is n-propyl.

17. The compound of claim 2 in which R is allyl.

18. A compound of claim 2 in which $R^2$ is amino, V is C—$CF_3$, and X is fluoro.

19. The compound of claim 18 in which R is 2-methylpropyl.

20. A herbicidal composition comprising an herbicidally effective amount of a compound of claim 1 in admixture with an agriculturally acceptable carrier.

21. The method of controlling undesired plant growth which comprises applying to the locus where control is desired a herbicidally effective amount of a composition of claim 20.

* * * * *